(12) United States Patent
Nagato et al.

(10) Patent No.: US 6,310,255 B1
(45) Date of Patent: Oct. 30, 2001

(54) PROCESS FOR PRODUCING HINOKITIOL

(75) Inventors: Yasuhiro Nagato; Katsuya Shimizu; Shinichi Yamamoto, all of Nobeoka (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 09/649,806

(22) Filed: Aug. 28, 2000

(30) Foreign Application Priority Data

Mar. 30, 1998 (JP) .................................... 10-084093
Mar. 29, 1999 (WO) .................................. PCT/JP99/01583

(51) Int. Cl.$^7$ ............................................... C07C 49/547
(52) U.S. Cl. ............................................................ 568/303
(58) Field of Search ................................... 568/303, 820, 568/823

(56) References Cited

FOREIGN PATENT DOCUMENTS

| | | |
|---|---|---|
| B-51-33901 | 9/1976 | (JP) . |
| 54-63063 | 5/1979 | (JP) . |
| 62-93250 | 4/1987 | (JP) . |
| 63-17841 | 1/1988 | (JP) . |
| 63-5049 | 1/1988 | (JP) . |
| B-4-27215 | 5/1992 | (JP) . |
| 6-239779 | 8/1994 | (JP) . |
| 8-40971 | 2/1996 | (JP) . |
| 520341 | 7/1976 | (RU) . |

OTHER PUBLICATIONS

O. Achmatowitz Jr. et al., "Stereoselective Synthesis Of Methyl β–DL–Novioside," Tetrahedron. vol. 32, pp. 1051–1054, 1976.

M.G. Banwell et al., "The Palladium–mediated Cross–coupling of Bromotropolones with Organostannanes; Application to Concise Syntheses of β–Dolabrin, β–Thujaplicin, 7–Methoxy–4–isopropyltropolone, and β–Thujaplicinol," J. Chem Soc. Chem. Commun., vol. 10, pp. 616–617, 1989.

M. Akimoto et al., "Formation of Ethylcyclopentadiene and the Reaction Mechanish in Vapor–Phase Reaction of Cyclopentadieme with Ethylene over Silicon Carbide (with English Abstract)," Bull. Jap. Chem. Soc., 1977(3), pp. 375–381, 1977.

Izv. Vyssh. Vchebn. Zaved., Khim Khim. Technol., 19(10), pp. 1511–1514, 1970.

R. Riemschneider et al., Montasch. Chemie., vol. 91, pp. 805–811, 1960.

S. McLean et al., "Substitution in the CyclopentaDienide Anion Series: Methylation Of The Cyclopentadienide And Methylcyclopentadiende Anions," Tetrahedron, vol. 21, pp. 2313–2327, 1965.

Primary Examiner—Johann Richter
Assistant Examiner—Sikarl A. Witherspoon
(74) Attorney, Agent, or Firm—Pennie & Edmonds LLP

(57) ABSTRACT

A process for producing hinokitiol which comprises the step of obtaining 1-isopropylcyclopentadiene from cyclopentadiene and an isopropylating agent represented by the general formula R—X wherein R is an isopropyl group and X is a halogen or the like (first step), reacting it with a dihaloketene to obtain a ketene adduct (second step), and decomposing the ketene adduct (third step), said first step comprising the following three steps:

a) a preparation step of cyclopentadienyl metal;
  b) a step of obtaining isopropylcyclopentadiene by isopropylating the cyclopentadienyl metal in an aprotic polar solvent; and
  c) a step of isomerizing 5-isopropylcyclopentadiene in the product selectively to 1-isopropylcyclopentadiene with heat.

18 Claims, No Drawings

PROCESS FOR PRODUCING HINOKITIOL

This application is a continuation of PCT International application PCT/JP99/01583 filed Mar. 29, 1999.

TECHNICAL FIELD

The present invention relates to a process for producing hinokitiol (another name: β-thujaplicin).

Hinokitiol produced in the present invention has not only antimicrobial and antifungal effect on a wide spectrum of bacteria and fungi but also cell-activating effect, inhibitory effect on tyrosinase activity, inhibitory effect on ethylene production in plants, etc. It is effective as an antimicrobial and antifungal agent when incorporated into medicines, cosmetics, hair tonics, shampoos or soaps, and it is incorporated also into freshness-maintaining films, antimicrobial coating materials, etc.

BACKGROUND ART

As processes for producing hinokitiol, the following processes have been known:

(i) a process in which hinokitiol is produced from methoxytropylidene via isopropyltropone and aminoisopropyltropone (Tetrahedron., 32, 1051 (1991));

(ii) a process in which hinokitiol is produced through 6 steps such as acetalization after epoxidation of carvone with hydrogen peroxide (JP-A-62-93250);

(iii) a process in which hinokitiol is produced by converting isopropylcyclohexanone or isopropylcyclohexenone to cyanohydrin, and then synthesizing isopropylcycloheptanone through two steps, followed by oxidation, bromination and dehydrobromination (JP-A-63-5048 and JP-A-63-17841); and (iv) a process of reacting bromotropolone with an organotin compound, followed by reduction with hydrogen in the presence of Pd/C catalyst (J. Chem. Soc., Chem. Commun., 1989, 616 (1989)).

These processes cannot be industrially practical because they comprise many steps or the starting materials are difficult to obtain.

As another production process, there is known a process of obtaining isopropylcyclopentadiene by the use of cyclopentadiene as a starting material, adding a dichloro-ketene to the isopropylcyclopentadiene, and subjecting the adduct to solvolysis. This process is industrially advantageous because the starting cyclopentadiene is easily available and the process comprises a small number of steps. It is known that in this process, hinokitiol is produced only from 1-isopropylcyclopentadiene among three isomers of isopropylcyclopentadiene. Therefore, investigations are conducted in order to increase the yield of the desired compound hinokitiol or reduce the troublesomeness of a purification step, by selectively synthesizing 1-isopropylcyclopentadiene. That is, the production of 1-isopropylcyclopentadiene with high selectivity is important in hinokitiol production.

As such a process, there are, for example, the following processes:

(v) a process in which hinokitiol is produced by reacting cyclopentadiene with a Grignard reagent (ethylmagnesium bromide) and isopropyl tosylate to obtain 1-isopropylcyclopentadiene with high selectivity, adding a dichloroketene to the 1-isopropylcyclopentadiene, and subjecting the adduct to solvolysis (JP-B-51-33901); and (vi) a process in which hinokitiol is produced by reacting cyclopentadiene with acetone under basic conditions to obtain 6,6-dimethylfulvene, reducing the 6,6-dimethylfulvene with a dialkylaluminum hydride to obtain 1-isopropylcyclopentadiene selectively, adding a dichloroketene to the 1-isopropylcyclopentadiene, and subjecting the adduct to solvolysis (JP-A-8-40971).

These processes are superior to the above processes (i) to (iv) because hinokitiol is obtained by fewer steps by using easily available and inexpensive cyclopentadiene as a starting material. But, they have the following defects: since a reagent requiring extreme nonaqueous conditions (i.e. the Grignard reagent in (v) or the dialkylaluminum hydride in (vi)) should be used, great precautions are necessary in handling the reagent; a solvent to be used and the like should be subjected to a special dehydration procedure; and these reagents are generally expensive. Thus, these processes for producing hinokitiol via 1-isopropylcyclopentadiene are also industrially disadvantageous.

The present inventors found that among isomers of isopropylcyclopentadiene, 5-isopropylcyclopentadiene is isomerized selectively to 1-isopropylcyclopentadiene by heat near room temperature. That is, the present inventors found that for hinokitiol production, it is important to synthesize 5- or 1-isopropylcyclopentadiene or a mixture thereof with high selectivity by the use of inexpensive and easily handleable reagents, while inhibiting the production of 2-isopropylcyclopentadiene as much as possible.

It is generally known that as described above, an alkylcyclopentadiene has three isomers 5-, 1- and 2-alkylcyclopentadienes due to the positions of the alkyl group. In a thermodynamically stable equilibrium state, an alkylcyclopentadiene is an isomer mixture consisting of substantially equal amounts of the 1-isomer and the 2-isomer and a small amount of the 5-isomer.

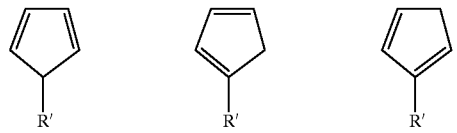

5-Alkylcyclopentadiene  1-Alkylcyclopentadiene  2-Alkylcyclopentadiene

The following various processes for producing an alkylcyclopentadiene by alkylating cyclopentadiene have been known though they are not a process for producing hinokitiol:

(vii) a process of reacting cyclopentadiene with an aliphatic lower alcohol in the presence of a catalyst in a vapor phase (JP-B-4-27215) and a process of reacting cyclopentadiene with ethylene on a hydrocarbon in a vapor phase (Journal of Chemical Society of Japan, 1977 (3), p. 375 (1977));

(viii) a process of reacting cyclopentadiene with metallic sodium in liquid ammonia and then with an equal amount of an alkyl halide (Izv. Vyssh. Vchebn, Zaved., Khim. Khim. Technol., 19 (10), p. 1511 (1970));

(ix) a process of reacting cyclopentadiene with an alkyl halide in an aqueous metal hydroxide solution in the presence of a phase transfer catalyst such as a quaternary ammonium salt (U.S. Pat. No. 3,560,583) and a process of reacting cyclopentadiene with an alkali metal hydroxide in an organic solvent in the presence of a dehydrating agent such as calcium oxide to produce a cyclopentadienyl metal and reacting the cyclopentadienyl metal with an alkyl halide (Russian Patent No. 520341);

(x) a process in which a Grignard reagent (an alkylmagnesium bromide) is used as in the above prior art (v) and a 1-alkylcyclopentadiene is selectively obtained by reacting a Grignard reagent of cyclopentadiene with an alkyl halide or an alkylsulfuric acid (Montasch. Chemie., 91, 805-812 (1960));

(xi) a process in which as the first step in the production process of a prostaglandin, the 1-isomer is produced by obtaining cyclopentadienyllithium from cyclopentadiene and an alkyllithium and reacting the cyclopentadienyllithium with ethyl 7-bromoheptanoate (JP-B-53-33583);

(xii) a process in which the 1-isomer or 5-isomer is produced by obtaining a cyclopentadienyl metal solution from metallic sodium and cyclopentadiene in an organic solvent such as dimethoxyethane or diglyme and adding the solution dropwise to an alkylating agent (Tetrahedron, vol. 21, 2313 (1965));

(xiii) a process in which as the first step in the production process of a norbornene derivative, cyclopentadienylsodium is produced by reacting cyclopentadiene with sodium hydride in tetrahydrofuran solvent, and an alkylating agent is added dropwise to the cyclopentadienylsodium at a low temperature (described in the Referential Examples of JP-A-54-63063); and (xiv) a process in which as the first step in the production process of optically active cyclopentenediol, an alkylcyclopentadiene is obtained by reacting cyclopentadiene with an alkylating agent in the presence of a base (JP-A-6-239779). In this reference, substantially all kinds of alkylating agents are mentioned. As the base, there are mentioned a wide variety of alkali metals, alkaline earth metals, metal hydrides, alkali metal alkoxides, etc. As a solvent for the reaction, there are mentioned diethyl ether, n-hexane, tetrahydrofuran, N,N-dimethylformamide, dimethyl sulfoxide, etc. It is stated that any solvent may be used so long as it has no undesirable influence on the reaction, and solvents are mentioned with almost no restriction. However, in Examples, there is described only a case of reacting cyclopentadiene with sodium hydride in tetrahydrofuran solvent to produce cyclopentadienylsodium, and then adding an alkylating agent to the cyclopentadienylsodium. This process is exactly the same as the above prior art (xiii).

The process (vii) has the following defects: a special apparatus for the vapor-phase reaction is necessary; the yield of the monoalkyl compound is low because of the production of substituted derivatives having two or more alkyl groups; and the alkylcyclopentadiene obtained is an equilibrium mixture, namely, the process does not give the 5-isomer or the 1-isomer selectively. The process (viii) is disadvantageous in that handling of the reagents used is difficult and that the alkylcyclopentadiene obtained is an equilibrium mixture. The process (ix) does not use a reagent requiring precautions in its handling, such as metallic sodium or liquid ammonia, but it gives only an alkylcyclopentadiene mixture having an equilibrium composition.

The processes (x) to (xii) give the 5-isomer and/or the 1-isomer with high selectivity. However, the process (x) and the process (xi) are difficult to practice industrially because an expensive reagent requiring extreme nonaqueous conditions should be used in both processes, namely, the Grignard reagent should be used in (x) as in (v) and the alkyllithium should be used in (xi). The process (xii) uses metallic sodium and hence requires extreme nonaqueous conditions. Moreover, the reference for the process (xii) describes only a case of adding a primary alkyl group. As a result of investigation by the present inventors, it has been found that the selectivity of the 5-isomer and/or the 1-isomer is low when a secondary or tertiary alkyl group having a low reactivity, such as an isopropyl group is added. Therefore, the process (xii) cannot be adopted in the process for producing hinokitiol of the present invention.

As to the process (xiii), in Reference Example 1, there is described in detail a process comprising cooling a tetrahydrofuran solution of cyclopentadienylsodium prepared from sodium hydride and cyclopentadiene to −45° C. to −55° C., adding thereto a primary alkyl bromide, and stirring the resulting mixture at the same temperature for 1 hour and then at −30° C. to −45° C. for 4.5 hours. In Reference Example 1, the proportions of the resulting isomers determined by the position of the alkyl group are not described but it is stated in the main text that in the alkylation carried out in the invention, the 5-isomer produced at first isomerizes to the 1-isomer and the 2-isomer immediately.

However, in Example 1 of the prior art (xiv), it is stated that a primary alkyl bromide is added dropwise to a tetrahydrofuran solution of cyclopentadienylsodium prepared from sodium hydride and cyclopentadiene, at −50° C. This process is exactly the same as the process (xiii), but the 5-isomer is selectively obtained at a low temperature and the 1-isomer is selectively obtained by heating up to room temperature. There is no description about the production of the 2-isomer.

As described above, the description about the isomers in (xiii) is different from that in (xiv). As a result of investigation on Example of (xiv) by the present inventors, the products obtained by the reaction could not be identified as the isomers, respectively, by the $^1$H-NMR described in Example. Thus, it could not be confirmed that 5-alkylcyclopentadiene and/or 1-alkylcyclopentadiene can be obtained with high selectivity.

The process in Example of each of (xiii) and (xiv) uses sodium hydride. Since sodium hydride is a reagent which requires extreme nonaqueous conditions and is generally expensive, the process is very difficult to practice industrially. Investigation by the present inventors revealed that the addition of an isopropyl group as a secondary alkyl group according to this process gives only an isopropylcyclopentadiene mixture having such an equilibrium composition that the proportions of the 1-isomer and the 2-isomer is substantially equal. That is, the processes (xiii) and (xiv) cannot be applied to the production of hinokitiol.

As described above, there has been known no process for producing hinokitiol easily with high selectivity at low cost without extreme nonaqueous conditions.

DISCLOSURE OF THE INVENTION

The present invention provides a process for producing hinokitiol by synthesizing 1-isopropylcyclopentadiene from easily available cyclopentadiene, adding a dichloroketene to this 1-isopropylcyclopentadiene, and subjecting the adduct to solvolysis, wherein 1-isopropylcyclopentadiene is produced easily with high selectivity at low cost without extreme nonaqueous conditions.

As a result of earnest investigation on the problems described above, the present inventors have accomplished the present invention. That is, the present invention includes the aspects described below.

(1) A process for producing hinokitiol which comprises the steps of obtaining 1-isopropylcyclopentadiene from cyclopentadiene and an isopropylating agent represented by the general formula R—X wherein R is an isopropyl group and X is a halogen atom, a tosyl group or an alkylsulfonate group (first step), reacting the 1-isopropylcyclopentadiene with a dihaloketene to obtain a ketene adduct (second step), and decomposing the ketene adduct (third step), said first step comprising the following three steps:

a) a step of preparing a cyclopentadienyl metal from cyclopentadiene and at least one of a metal hydroxide or a metal alkoxide (preparation step of cyclopentadienyl metal);

b) a step of obtaining isopropylcyclopentadiene by reacting the cyclopentadienyl metal with the isopropylating agent in the presence of an aprotic polar solvent capable of forming two liquid phases when mixed with isopropylcyclopentadiene as a product (isopropylation step); and c) a step of isomerizing 5-isopropylcyclopentadiene in the isopropylcyclopentadiene selectively to 1-isopropylcyclopentadiene with heat (isomerization step).

(2) A process according to the above item (1), which further comprises a step of separating a phase composed mainly of isopropylcyclopentadiene, by taking out a lower layer after standing after the isopropylation step.

(3) A process according to the above item (1), wherein said aprotic polar solvent is dimethyl sulfoxide in the isopropylation step.

(4) A process according to the above item (1), wherein the metal hydroxide is used in the preparation step of cyclopentadienyl metal.

(5) A process according to the above item (1), wherein the metal hydroxide is potassium hydroxide in the preparation step of cyclopentadienyl metal.

(6) A process according to the above item (1), wherein the isopropylation step is carried out in the presence of an aliphatic hydrocarbon in addition to said aprotic polar solvent.

(7) A process according to any one of the above items (1) to (6), wherein said aprotic polar solvent is used in an amount of 4 moles or more per mole of the cyclopentadienyl metal in the isopropylation step.

(8) A process according to any one of the above items (1) to (7), wherein said aprotic polar solvent is used in an amount of 6 moles or more per mole of the cyclopentadienyl metal in the isopropylation step.

(9) A process according to any one of the above items (1) to (5), wherein in the isopropylation step, said aprotic polar solvent is used in an amount of 10 moles or more per mole of the cyclopentadienyl metal, and a solution containing the cyclopentadienyl metal is added to the isopropylating agent.

(10) A process according to the above item (1), wherein in the isopropylation step, said metal alkoxide is potassium ethoxide and said aprotic polar solvent is used in an amount of 12 moles or more per mole of the cyclopentadienyl metal.

(11) A process according to any one of the above items (1) to (9), wherein a reaction temperature is not higher than 30° C. in the isopropylation step.

(12) A process according to any one of the above items (1) to (11), wherein an amount of water present in the reaction system is not more than 3 moles per mole of the cyclopentadienyl metal in the isopropylation step.

(13) A process according to any one of the above items (1) to (12), wherein the preparation step of cyclopentadienyl metal and the alkylation step are carried out in an inert gas atmosphere.

(14) A process according to any one of the above items (1) to (13), wherein a temperature at the isomerization step is 0° C. to 40° C.

(15) A process according to any one of the above items (1) to (14), wherein in the third step, the decomposition of a ketene adduct is carried out in the presence of triethylamine, water and a water-soluble organic solvent while adding triethylamine dropwise to the reaction system.

(16) A process according to the above item (15), wherein the decomposition of the ketene adduct is carried out by further adding at least one organic acid selected from the group consisting of formic acid, acetic acid and propionic acid.

(17) A process according to the above item (15) or (16), wherein said water-soluble organic solvent is tertiary butanol.

(18) A process according to any one of the above items (1) to (17), wherein a portion of an apparatus used in the third step and a hinokitiol purification step which is brought into contact with hinokitiol is made of at least one material selected from the group consisting of Hastelloy C, glass, resins and ceramics.

The process for producing hinokitiol of the present invention is chemically formulated as follows:

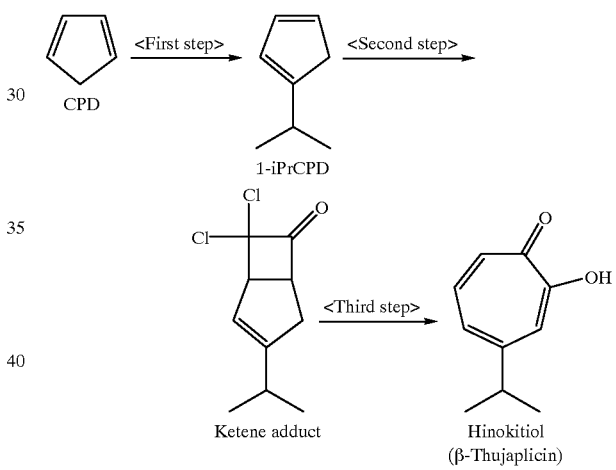

*CPD: Cyclopentadiene
1-iPrCPD: 1-Isopropylcyclopentadiene

As described above, only 1-isopropylcyclopentadiene can be converted to hinokitiol and hinokitiol cannot be produced from 2-isopropylcyclopentadiene or 5-isopropylcyclopentadiene.

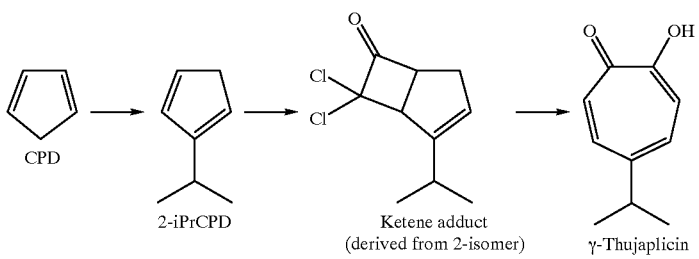

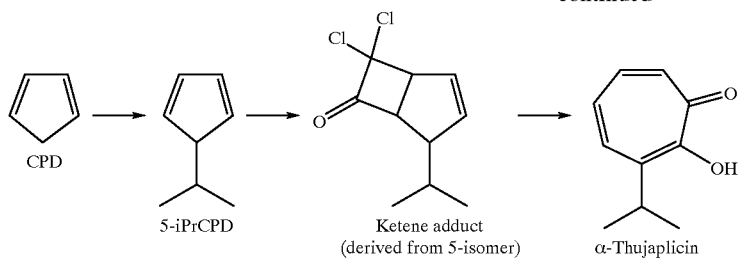

The first step is chemically formulated as follows:

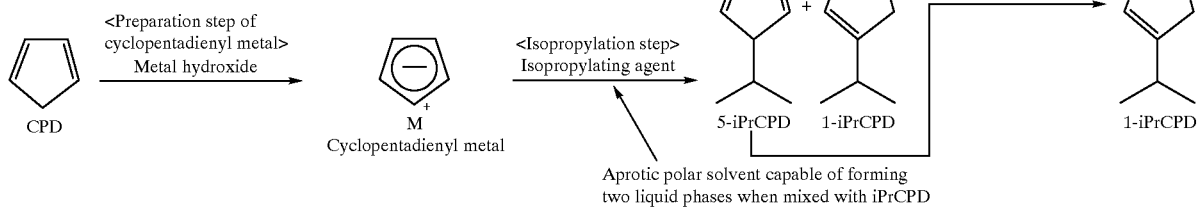

As described above as prior art, a process for producing hinokitiol via 1-isopropylcyclopentadiene and a ketene adduct by using cyclopentadiene as a starting material has already been known.

In general, an alkylcyclopentadiene has three isomers, i.e., 1-isomer, 2-isomer and 5-isomer owing to the differences of positions of the double bonds and the alkyl group. It is known that when a cyclopentadienyl metal is obtained from cyclopentadiene and a base and reacted with an alkylating agent, the 5-isomer is produced at first and then isomerizes to the 1-isomer and 2-isomer, which exist in substantially equal amounts together with a small amount of the 5-isomer at an equilibrium state.

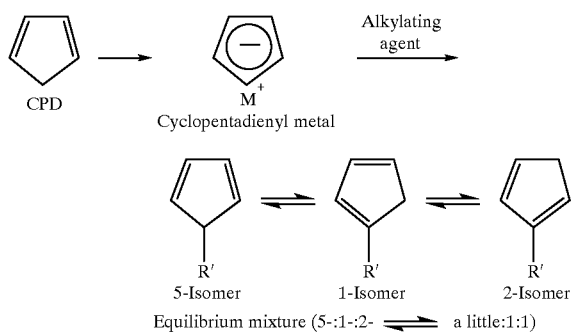

V. A. Mironov et al. revealed the following: alkyl addition to a cyclopentadienyl metal gives the 5-isomer at first; the hydrogen atom on the carbon atom of the 5-isomer to which the alkyl group is bonded undergoes 1,2-hydrogen transfer to the adjacent carbon atom, resulting in isomerization to the 1-isomer; and similarly, the methylene proton of the 1-isomer undergoes 1,2-hydrogen transfer to the adjacent carbon atom, resulting in isomerization to the 2-isomer. In addition, they also revealed that the isomerization of the 5-isomer to the 1-isomer proceeds even at a lower temperature but that the isomerization of the 1-isomer to the 2-isomer requires a higher temperature (Tetrahedron, vol. 19, 1939 (1963)).

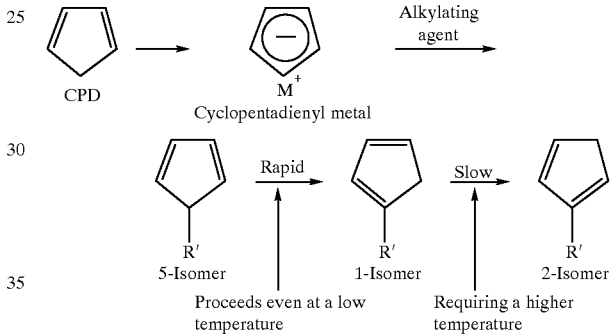

Therefore, in the case of the isomerization which proceeds owing to 1,2-hydrogen transfer, it is possible to produce the 5-isomer and/or the 1-isomer while minimizing the production of the 2-isomer. S. McLean et al. state that the above isomerization by 1,2-hydrogen transfer is effective in the absence of a strong base, and that in the presence of a strong base, an alkylcyclopentadienyl anion is produced from the 5-isomer and isomerizes directly to an equilibrium mixture (Tetrahedron, vol. 21, pp. 2313–2329 (1965)).

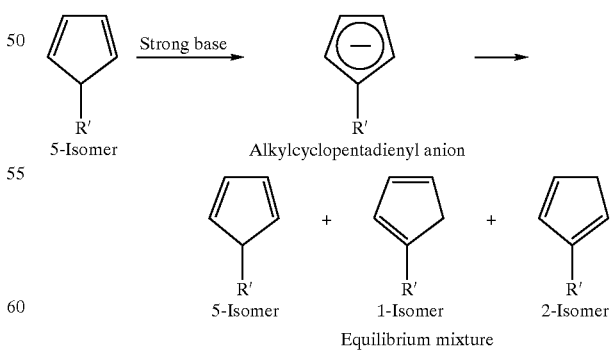

That is, in the presence of a strong base, selective synthesis of the 5-isomer and/or the 1-isomer is impossible and an equilibrium mixture of substantially equal amounts of the 1-isomer and the 2-isomer is formed. Accordingly, in other words, preventing the contact of the produced alkylcyclopentadine with a strong base is absolutely necessary for synthesizing the 5-isomer and/or the 1-isomer selectively.

The term "strong base" used herein means a cyclopentadienyl metal such as cyclopentadienylsodium obtained from metallic sodium and cyclopentadiene. In the prior art processes (viii) and (ix), the 5-isomer or the 1-isomer, or both are selectively obtained by the use of a Grignard reagent of cyclopentadiene or a cyclopentadienyl metal such as cyclopentadienyllithium in a homogeneous solvent. The present inventors conjecture as follows: the reason for this selective synthesis is that no alkylcyclopentadienyl anion is produced because of the low basicity of such a cyclopentadienyl metal. When the metal of a cyclopentadienyl metal is an alkali metal such as sodium, the cyclopentadienyl metal itself is a strong base capable of accelerating the isomerization to an equilibrium composition, though it is necessary as a reactant in the system. Therefore, some consideration is needed for carrying out the reaction.

In the prior art (xii), S. McLean et al. obtain the 5-isomer and/or the 1-isomer with high selectivity by adding a solution of cyclopentadienylsodium in dimethoxyethane or diglyme dropwise to an alkylating agent. The present inventors conjecture that the isomerization to an equilibrium composition via an alkylcyclopentadienyl anion is prevented by preventing the substantial presence of free cyclopentadienylsodium in the system by causing alkylation simultaneously with the dropwise addition. When the reaction is carried out by the reverse dropwise addition, i.e., the dropwise addition of the alkylating agent to the cyclopentadienylsodium solution, the alkylcyclopentadiene produced during the dropwise addition comes into contact with free cyclopentadienylsodium, so that only alkylcyclopentadiene having an equilibrium composition or a high 2-isomer content can be obtained. The process in Example of the prior art (xiii) and that in Example of the prior art (xiv) are the same. In these processes, an alkylating agent is added dropwise to a cyclopentadienylsodium solution, namely, the dropwise addition is reverse to that in the above prior art (xii). The ratio among isomers of the resulting alkylcyclopentadiene described in (xiii) and that described in (xiv) are different. In (xiii), it is stated that the 5-isomer isomerizes to the 1-isomer and the 2-isomer immediately. In (xiv), it is stated that the 5-isomer or the 1-isomer can be obtained with high selectivity. Judging from the order of dropwise addition, the description in (xiii) seems correct, however if the 5-isomer and the 1-isomer are obtained with high selectivity by the process (xiv), the reason is unknown.

The following is conjectured: for obtaining the 5-isomer and/or the 1-isomer selectively by the prior art (xii), it is necessary that the reaction of the cyclopentadienylsodium added dropwise with the alkylating agent should be rapid, namely, the reactivity of the alkylating agent should be high. The reason is as follows: it can be speculated that for example, even when the reaction is carried out according to the prior art process (xii), cyclopentadienylsodium is substantially present in the system if the reactivity of the alkylating agent is low, and that since the reaction system is homogeneous, this strong base comes into contact with the product alkylcyclopentadiene, so that the isomerization via an alkylcyclopentadienyl anion proceeds. In fact, only the addition of a primary alkyl group such as a methyl group is described in the prior art (xii). When the present inventors carried out the alkylation according to such a prior art, employment of a primary alkylating agent such as dimethyl sulfate or n-propyl bromide gave the 5-isomer and/or the 1-isomer selectively, but employment of isopropyl bromide, a secondary alkyl halide having a low reactivity gave isopropylcyclopentadiene as a mixture of substantially equal amounts of the 1-isomer and the 2-isomer. The prior art process (xiv) is similar to the prior art process (xii) in that cyclopentadienylsodium, a strong base is used in a homogeneous reaction system, though the reason for the highly selective production of the 5-isomer and/or the 1-isomer is unknown. All of the three alkyl groups described in Examples of the prior art (xiv) are primary alkyl groups and no addition of a secondary or tertiary alkyl group having a low reactivity is described therein. When the present inventors synthesized isopropylcyclopentadiene according to the prior art process (xiv), only an equilibrium mixture of substantially equal amounts of the 1-isomer and the 2-isomer could be obtained as in the case of (xii). The investigation results obtained are shown in the Comparative Example 10 hereinafter described.

The present inventors investigated a process which uses a strong base such as cyclopentadienylsodium or cyclopentadienylpotassium and can inhibits the isomerization via an alkylcyclopentadienyl anion even in the case of the reaction with a secondary alkylating agent having a low reactivity. Consequently, it was found that the 5-isomer and/or the 1-isomer can be selectively obtained by using an organic solvent capable of forming two liquid phases when mixed with the product alkylcyclopentadiene.

That is, the following was found: although the reaction of cyclopentadienylsodium or cyclopentadienylpotassium with the alkylating agent takes place in the aforesaid solvent, the alkylcyclopentadiene produced by the reaction immediately undergoes phase separation from the solvent, and the phase separation prevents the contact of the product alkylcyclopentadiene with the strong base such as cyclopentadienylsodium or cyclopentadienylpotassium, so that no isomerization via an alkylcyclopentadienyl anion takes place, resulting in the selective production of the 5-isomer and/or the 1-isomer.

The following was also found: in such a process, unlike in the prior art (xii), the reactivity of the alkylating agent does not affect the selectivity of the 5-isomer and/or the 1-isomer at all, the order of dropwise addition of the reagents has no influence on the selectivity, and no special consideration is necessary for carrying out the reaction. This can be understood from the principle that the contact of the product alkylcyclopentadiene with the strong base such as cyclopentadienylsodium is prevented by the phase separation. In practice, it was found that the 5-isomer and/or the 1-isomer can be selectively obtained even by reacting an alkylating agent such as isopropyl bromide which does not bring about the selectivity in the prior arts (xii) and (xiv).

There has not been known the above-mentioned concept that the selectivity of the 5-isomer and/or the 1-isomer is increased by preventing the contact of the product alkylcyclopentadiene with the strong base such as cyclopentadienylsodium or cyclopentadienylpotassium by the phase separation. This concept was formed for the first time as a result of earnest investigation by the present inventors. A reaction in a homogeneous system is carried out in all prior arts for obtaining the 5-isomer and/or the 1-isomer selectively, and there has been no process in which the selectivity of the 5-isomer and/or the 1-isomer is correlated with the states of one or more phases where reaction is carried out.

Furthermore, it is a more remarkable advantage of the present invention that even if water is present in the reaction system, water have very slight influence on the selectivity of the 5-isomer and/or the 1-isomer. All the prior arts for selectively obtaining the 5-isomer and/or the 1-isomer require extreme nonaqueous conditions and are difficult to practice industrially. In the present invention, the selectivity is not much lowered even if water is present. Therefore, it is not necessary to use a substance which is expensive and is difficult to handle industrially, such as a single alkali metal or an alkali metal hydride, and a metal hydroxide can be suitably used which is inexpensive and is easy to handle. In practice, when a metal hydroxide is used, water is produced in an amount equimolar with that of the metal hydroxide during the preparation of a cyclopentadienyl metal. Even if water is contained as a contaminant in addition to the water produced during the preparation, the selectivity of the 5-isomer and/or the 1-isomer can be kept high. A Grignard reagent or a lithium compound decomposes in the presence of water, so that no reaction takes place. In the prior art (xii), the alkylation is retarded by the presence of water, so that a strong base such as cyclopentadienylsodium is substantially present in the system, resulting in isomerization to an equilibrium composition. Therefore, there cannot be used a metal hydroxide which gives water during the preparation of a cyclopentadienyl metal, and a solvent to be used should be subjected to a special dehydrating procedure. The production of the 5-isomer and/or the 1-isomer with high selectivity by the use of a metal hydroxide has not been reported and has been achieved for the first time by employing the phase separation method according to the present invention.

For exactly the same reason as above, a metal alkoxide can be used for preparing a cyclopentadienyl metal. In this case, an alcohol is produced in an amount equimolar with that of the metal during the preparation of the cyclopentadienyl metal, but the alcohol produced does not lower the selectivity in the reaction system involving phase separation according to the present invention, though it retards the alkylation reaction to lower the selectivity of the 5-isomer and/or the 1-isomer in a homogeneous reaction such as that employed in the prior art (xii).

The process disclosed in the prior art (ix), i.e., the process comprising reacting cyclopentadiene in an aqueous solution of a metal hydroxide such as sodium hydroxide in the presence of a phase transfer catalyst such as a quaternary ammonium salt to prepare cyclopentadienylsodium, and adding an alkyl. halide to the cyclopentadienylsodium is utterly different in reaction system from the process of the present invention. Two liquid phases are formed also in the prior art (ix) but before the addition of an alkylating agent, they are an aqueous phase composed of water and a metal hydroxide and an organic phase composed of cyclopentadiene and cyclopentadienylsodium, and the aqueous phase is a lower phase when the two phases are allowed to stand. When the alkylating agent is added to them, it reacts with cyclopentadienylsodium in the organic phase and the resulting alkylcyclopentadiene remain as it is in the organic phase. Therefore, the product alkylcyclopentadiene comes into contact with cyclopentadienylsodium in the organic phase, so that isomerization via an alkylcyclopentadienyl anion takes place. Consequently, only an equilibrium composition of the 1-isomer and the 2-isomer in almost the same amount can be obtained.

The reaction system according to the present invention is different from that of the prior art (ix) in the constituents of the phases. In said reaction system, when an alkylating agent is added to a homogeneous phase composed of a cyclopentadienyl alkali metal and an organic solvent, the resulting alkylcyclopentadiene immediately undergoes phase separation to form an alkylcyclopentadiene phase, so that the contact of the alkylcyclopentadiene with the cyclopentadienyl alkali metal is broken off.

There is no prior art in which the 5-isomer or the 1-isomer, or both are obtained with high selectivity by using at least one material selected from metal hydroxides or metal alkoxides. When a metal hydroxide is used, the resulting alkylcyclopentadiene has been only an equilibrium mixture of substantially equal amounts of 1-alkylcyclopentadiene and 2-alkylcyclopentadiene.

According to the present invention, there is provided a process for producing hinokitiol by obtaining 1-isopropylcyclopentadiene from cyclopentadiene, adding a dihaloketene to the 1-isopropylcyclopentadiene, and subjecting the resulting ketene adduct to solvolysis, which process permits preparation of 1-isopropylcyclopentadiene with high selectivity at low cost by a simple procedure without extreme nonaqueous conditions, and hence permits production of hinokitiol with high selectivity at low cost by a simple procedure without extreme nonaqueous conditions.

BEST MODE FOR CARRYING OUT THE INVENTION

The first step according to the present invention is explained below at first. The preparation step of cyclopentadienyl metal is a step of preparing a cyclopentadienyl metal by reacting cyclopentadiene with a metal hydroxide or a metal alkoxide in a solvent. In practice, the cyclopentadienyl metal is ionized into a cyclopentadienyl anion and a metal ion and dissolved in the solvent. The metal hydroxide or the metal alkoxide acts as a base which takes a hydrogen atom away from cyclopentadiene. The simple metal or metal hydride described in the prior arts may be used as a base in place of the metal hydroxide or the metal alkoxide used in the present invention, but they are disadvantageous as compared with the metal hydroxide in that as described in BACKGROUND ART, precautions are necessary in handling them because they tend to ignite on reaction with water in the air. In the present invention, at least one base selected from metal hydroxides or metal alkoxides is used as a base in the preparation step of cyclopentadienyl metal.

The metal hydroxide used in the present invention is an alkali metal hydroxide or an alkaline earth metal hydroxide and includes, for example, lithium hydroxide, sodium hydroxide, potassium hydroxide, rubidium hydroxide, caesium hydroxide, magnesium hydroxide, calcium hydroxide and barium hydroxide. Of these, sodium hydroxide or potassium hydroxide is preferable. However, sodium hydroxide often forms a precipitate in the preparation of a cyclopentadienyl metal by the reaction of sodium hydroxide with cyclopentadiene. In this case, potassium hydroxide is preferably used. When potassium hydroxide is used in the form of any of flakes, particles and an aqueous solution, it may be commercially available one. The metal alkoxide used in the present invention includes, for example, sodium ethoxide, sodium methoxide, potassium ethoxide and potassium methoxide, and is preferably potassium ethoxide. The metal hydroxide is preferable to the metal alkoxide in view of handleability and price in the industrial production.

As the solvent used for preparing the cyclopentadienyl metal, any solvent may be used so long as it dissolves the cyclopentadienyl metal. The solvent need not be subjected to a special treatment such as drying. However, when there is used a solvent having an undesirable influence on the reaction of the cyclopentadienyl metal with an isopropylating agent in the subsequent isopropylation step, a step of distilling off the solvent should be added after the preparation of the cyclopentadienyl metal and before the reaction of the cyclopentadienyl metal with an isopropylating agent, resulting in a complicated process. Therefore, the same solvent as used in the subsequent isopropylation step is preferably used also for the preparation of the cyclopentadienyl metal because the step of distilling off the solvent can be omitted.

The ratio between the amounts of cyclopentadiene and the metal hydroxide(s) or the metal alkoxide(s) is not particularly limited. The molar ratio of the metal hydroxide(s) or the metal alkoxide(s) to cyclopentadiene ranges usually from 0.1 to 10, preferably from 0.5 to 2, more preferably from 0.8 to 1.5.

As the reaction temperature in the preparation of the cyclopentadienyl metal, a temperature in a range of −10° C. to the boiling temperature of the solvent may be employed. When the reaction temperature is too low, the reaction does not proceed easily. When the reaction temperature is too high, the dimerization of cyclopentadiene proceeds, so that dicyclopentadiene tends to be produced. Therefore, the reaction temperature is preferably 0° C to 80° C., more preferably 10° C. to 50° C. The reaction can be carried out at atmospheric pressure or under pressure. The boiling point of cyclopentadiene at atmospheric pressure is about 40° C., and therefore in an open system at atmospheric pressure, the reaction is preferably carried out in a reactor equipped with a reflux condenser, in order to prevent the loss of cyclopentadiene. Since the reaction of cyclopentadiene with the metal hydroxide(s) or the metal alkoxide(s) is exothermic, the reactor is preferably equipped with a means for maintaining a predetermined reaction temperature. Since the cyclopentadienyl metal is apt to be oxidized by oxygen in the air, the reaction system is preferably sealed up with an inert gas such as nitrogen. The reaction time is usually 10 inutes to 6 hours. When the same solvent as used in the subsequent isopropylation step is used for the preparation of the cyclopentadienyl metal, the solution of the cyclopentadienyl metal obtained in the preparation step can be used as it is in the isopropylation step without any after-treatment. The water or alcohol produced by the reaction in the preparation step of cyclopentadienyl metal may be separated and removed before carrying out the isopropylation step. For example, when a solvent having a boiling point higher than that of water or the alcohol is used, the water or alcohol can be removed by distillation.

The isopropylation step is a step of obtaining isopropylcyclopentadiene by the reaction of an isopropylating agent with the cyclopentadienyl metal obtained in the preceding step.

The isopropylating agent used in the isopropylation step is represented by the general formula R—X. In the formula, R is an isopropyl group and X is a halogen atom, a tosyl group or an alkylsulfonate group. The isopropylating agent includes, for example, isopropyl chloride, isopropyl bromide, isopropyl iodide, isopropyl tosylate and diisopropylsulfuric acid.

The solvent used in the isopropylation step is one which forms two liquid phases when mixed with the product isopropylcyclopentadiene and dissolves the cyclopentadienyl metal. In the reaction of the cyclopentadienyl metal with the isopropylating agent, the nucleophilic attack of the cyclopentadienyl anion of the cyclopentadienyl metal on the alkylating agent is the first stage, and hence it is preferable to use a solvent which hardly solvates the cyclopentadienyl anion. Therefore, it is preferable to use a solvent which has no acidic hydrogen atom capable of participating in a hydrogen bond, hardly solvates anions, and dissolves the cyclopentadienyl metal by remarkably solvating the metal ion of the cyclopentadienyl metal by its high polarity, namely, an aprotic polar solvent which forms two liquid phases when mixed with the product alkylcyclopentadiene. Such a solvent includes sulfone compounds and sulfoxide compounds. Specific examples thereof are sulfolane, dimethyl sulfoxide, diethyl sulfoxide, etc. Of these, dimethyl sulfoxide (hereinafter abbreviated as DMSO) is preferable. When there is used an aprotic polar solvent which does not form two liquid phases even when mixed with alkylcyclopentadiene as a product, 5-isopropylcyclopentadiene and/or 1-isopropylcyclopentadiene cannot be obtained with high selectivity. For example, acetonitrile, tetrahydrofuran, demethylformamide, hexamethylphosphortriamide or 1,3-dimethyl-2-imidazolidinone is a typical aprotic polar solvent but does not form two liquid phases when mixed with the product isopropylcyclopentadiene. Therefore, when such a solvent is used, 5-isopropylcyclopentadiene and/or 1-isopropylcyclopentadiene cannot be obtained with high selectivity.

It is effective to use a hydrocarbon solvent by its supplementary addition in order to assist the phase separation between the product isopropylcyclopentadiene and the solvent capable of forming two liquid phases when mixed with isopropylcyclopentadiene. As such a solvent, an aliphatic hydrocarbon is preferable, but it is not preferable to use a hydrocarbon solvent which forms a homogeneous phase together with the solvent capable of forming two liquid phases when mixed with isopropylcyclopentadiene. When a hydrocarbon having too low a boiling point is used, a great loss thereof is made during operations. Therefore, an aliphatic hydrocarbon having 6 or more carbon atoms is more preferable. The aliphatichydrocarbon may be either linear or branched. Preferable examples thereof are hexane, heptane, octane, cyclohexane, etc. A solvent other than those described above may be co-used so long as it does not lessen the effect of the present invention.

The used amount of the aprotic polar solvent capable of forming two liquid phases when mixed with the product isopropylcyclopentadiene is important. For obtaining the desired isomer(s) of isopropylcyclopentadiene with high selectivity, the using amount is 4 moles or more, preferably 6 moles or more, per mole of the cyclopentadienyl metal. When the amount is less than 4 moles, the amount of 2-isopropylcyclopentadiene produced tends to be increased. The reason is not clear. The present inventor guess the reason as follows: when the amount of the solvent is too small, the amount of the cyclopentadienyl metal contained in the isopropylcyclopentadiene phase is increased as much. Particularly when a solution of the cyclopentadienyl metal is added dropwise to the isopropylating agent without supplementary addition of a hydrocarbon, the amount of the aprotic polar solvent used is preferably 10 moles or more. When potassium ethoxide is used, the amount of the aprotic polar solvent used is preferably 12 moles or more per mole of the cyclopentadienyl metal. The fact that the ratio among isomers of isopropylcyclopentadiene varies depending on the amount of the solvent used is not found in the homogeneous reaction employed in any prior art and is thought to be a phenomenon characteristic of the progress of the isopropylation step according to the present invention by the two-phase reaction.

The reaction in the isopropylation step proceeds while forming the following two phases (phase A and phase B):
Phase A: a phase composed mainly of isopropylcyclopentadiene, or a phase composed mainly of isopropylcyclopentadiene and a hydrocarbon optionally added.
Phase B: a phase composed mainly of the solvent capable of forming two liquid phases when mixed with isopropylcyclopentadiene and the cyclopentadienyl metal.

The isopropylating agent reacts with the cyclopentadienyl metal in phase B, and isopropylcyclopentadiene produced by the reaction transfers to phase A immediately and hence does not come into contact with the cyclopentadienyl metal, a strong base.

The ratio between the amounts of the cyclopentadienyl metal and the isopropylating agent is not particularly limited. The molar ratio of the isopropylating agent to the cyclopentadienyl metal is usually 0.1 to 10, preferably 0.5 to 3, more preferably 0.8 to 1.2. When the molar ratio is less than 1 in the prior art (xii), the cyclopentadienyl metal is present in an unreacted state in the reaction system, so that the 5-isomer and/or the 1-isomer cannot be obtained with high selectivity. However, in the present invention, there is not such a restriction because the phase separation is utilized. This fact means that the operating latitude in the reaction is wide, and it is advantageous particularly when the reaction is continuously carried out.

The reaction temperature in the isopropylation step ranges from −20° C. to 30° C., preferably from −10° C. to 25° C., more preferably from −5° C. to 10° C. When the reaction temperature is lower than −20° C., the reaction is slow. When the reaction temperature is higher than 30° C., the amount of 2-isopropylcyclopentadiene produced is increased. For carrying out the reaction, the isopropylating agent may be added to a solution of the cyclopentadienyl metal dropwise or in small portions, or a solution of the cyclopentadienyl metal may be added to the isopropylating agent dropwise or in small portions. When the cyclopentadienyl metal is mixed with the isopropylating agent at a temperature lower than −20° C., the reaction may be carried out by raising the temperature to −20° C. to 25° C. When there is used a reactor in which the heat generated by the reaction can be effectively removed and the reaction temperature can be maintained in the above temperature range, it is possible to mix the cyclopentadienyl metal and the isopropylating agent all at once and cause the reaction at the same time. As such a reactor, there may be used a tubular reactor equipped with a stirring means such as a static mixer in which the cyclopentadienyl metal and the isopropylating agent can be reacted while feeding them to the reactor. Since the process of the present invention realizes highly selective production of the 5-isomer and/or the 1-isomer by the use of the phase-separation system, no special consideration is needed for carrying out the reaction, unlike in the prior art (xii).

The amount of water present in the reaction system, inclusive of water produced during the preparation of the cyclopentadienyl metal by the use of a metal hydroxide, is adjusted to not more than 3 moles, preferably not more than 2.5 moles, more preferably not more than 2 moles, per mole of the cyclopentadienyl metal. This is because when the amount of water is more than 3 moles, the selectivity of 5-isopropylcyclopentadiene and/or 1-isopropylcyclopentadiene is lowered. However, considering the fact that water is produced in an amount of 1 mole per mole of the cyclopentadienyl metal during the preparation of the cyclopentadienyl metal, the amount of water of 3 moles means that, before the preparation, water may be present in an amount of 2 moles per mole of the cyclopentadienyl metal, namely, it means wide permissible limits of the amount of water present in the reaction system. Therefore, in the present invention, the solvent and starting materials used need not be subjected to a special drying procedure, and this is markedly advantageous for using the solvent and the like after recovery.

When the reaction of the cyclopentadienyl metal with the isopropylating agent is carried out in a tank reactor, it is preferably carried out with stirring. The reaction is carried out at a degree of stirring of preferably 0.1 kW or more, more preferably 0.2 kW or more, per cubic meter of the reaction solution. This is because when the degree of stirring is less than 0.1 kW/m$^3$, the progress of the reaction is slowed down and moreover the selectivity of 5-isopropylcyclopentadiene and/or 1-isopropylcyclopentadiene is lowered.

During the isopropylation, the reaction system is preferably sealed up with an inert gas such as nitrogen. This is because the unreacted cyclopentadienyl metal is oxidized by oxygen in the air. When the oxidation takes place, insoluble materials are suspended near the liquid—liquid interface of the reaction solution composed of two liquid phases, in the after-treatment described below, so that layer separation becomes difficult in some cases.

The after-treatment after completion of the isopropylation is as follows. After completion of the reaction, the reaction solution is composed of two liquid phases. The lower phase is taken out at first and the upper phase containing an alkylcyclopentadiene is collected. For removing a slight amount of the alkali contained in the upper phase, the upper phase is repeatedly washed with water until the washings are no longer alkaline, or the upper phase is washed after being acidified with a mineral acid such as hydrochloric acid or sulfuric acid. In this case, a hydrocarbon such as hexane may be added. The lower phase may be taken out after a mineral acid is added to the reaction solution composed of two liquid phases after completion of reaction to acidify the whole system. The solution temperature during the after-treatment is also important and is preferably not higher than 30° C. This is because when the solution temperature is higher than 30° C., the amount of 2-isopropylcyclopentadiene produced tends to be increased during the after-treatment.

The isomerization step is a step of isomerizing 5-isopropylcyclopentadiene in the isopropylcyclopentadiene obtained in the isopropylation step to 1-isopropylcyclopentadiene with heat. Since no strong base such as the cyclopentadienyl metal is present in the liquid composed mainly of isopropylcyclopentadiene which is obtained by the after-treatment, the isomerization is achieved by 1,2-hydrogen transfer by heat. Although the isomerization of the 5-isomer to the 1-isomer by heat is a reversible reaction, a very small amount of the 5-isomer can be present after the isomerization because the equilibrium lies to the 1-isomer side. On the other hand, the isomerization of the 1-isomer to the 2-isomer also takes place and is also a reversible reaction. In the equilibrium composition, the ratio of the 1-isomer to the 2-isomer is approximately 1:1 as described above, but this isomerization is slower than the isomerization of the 5-isomer to the 1-isomer. Therefore, the 1-isomer can be obtained as a main product by allowing only the isomerization of the 5-isomer to the 1-isomer to proceed by maintaining a mixture of the 5-isomer and the 1-isomer at a certain temperature for a necessary period of time. In the isomerization, the liquid containing the 5-isomer and the 1-isomer may be either allowed to stand or stirred. The isomerization temperature ranges from 0° C. to 40° C. When the isomerization temperature is lower than 0° C., it is not practical because the progress of the isomerization is slow. When the isomerization temperature is too high, the progress of the isomerization is rapid but the production of the 2-isomer, an undesirable isomer is also accelerated and becomes difficult to control. Although the time required for the isomerization cannot be unequivocally determined because it varies depending on the temperature condition, the ratio among the isomers at the beginning of the isomerization, etc., it is substantially as follows. The isomerization time is approximately 8 to 40 hours at an isomerization temperature of 10° C., 3 to 30 hours at 20° C., or 30 minutes to 10 hours at 30° C. When the isomerization time is below the above range, the amount of the remaining 5-isomer is large. When the isomerization time is beyond the above range, the amount of the 2-isomer produced tends to be increased.

The above is the first step comprising the three steps, i.e., the preparation step of cyclopentadienyl metal, the isopropylation step and the isomerization step.

The second step according to the present invention is a step of adding a dihaloketene to the 1-isopropylcyclopentadiene obtained in the first step, to form a ketene adduct.

The dihaloketene is represented by the general formula CXY=C=O wherein X and Y are independently a halogen atom selected from chlorine, bromine and iodine. The dihaloketene includes, for example, dichloroketenes, dibromoketenes and chlorobromoketenes. Of these, the dichloroketenes are preferable.

Since the dihaloketene is very unstable, it is preferable to carry out ketene preparation and the ketene addition in one pot. As a method for preparing the ketene, either of the following two known methods may be adopted:

(i) a method of carrying out dehydrohalogenation by reacting triethylamine with a dihaloacetyl halide represented by the general formula $CHXY-COZ_1$ wherein X and Y are as defined above and $Z_1$ is a halogen atom selected from chlorine, bromine and iodine.

(ii) a method of carrying out dehalogenation by reacting metallic zinc powder with a trihaloacetyl halide represented by the general formula $CXYZ_2-COZ_1$ wherein X, Y and $Z_1$ are as defined above and $Z_2$ is a halogen atom selected from chlorine, bromine and iodine.

The second step according to the present invention is explained below by taking the case of the method for preparing the dihaloketene by dehydrohalogenation of a dihaloacetyl halide.

A dihaloacetyl halide is added to the isopropylcyclopentadiene obtained in the first step, and triethylamine is added dropwise to the mixture while maintaining a predetermined temperature range. Alternatively, a dihaloacetyl halide and triethylamine are added dropwise at the same time to the isopropylcyclopentadiene. In this case, triethylamine is preferably added dropwise, but not all at once. This is because when a predetermined amount of triethylamine is mixed with the isopropylcyclopentadiene all at once, 1-isopropylcyclopentadiene in the isopropylcyclopentadiene is isomerized to 2-isopropylcyclopentadiene owing to the basicity of triethylamine. Since triethylamine acts also as a polymerization catalyst for the ketene, it is preferable to prevent the presence of free triethylamine in the reaction system as sufficiently as possible by slowly adding triethylamine dropwise. Since the reaction in the second step is exothermic, the dropwise addition method is preferable also for maintaining the reaction temperature in a predetermined range.

The dihaloacetyl halide usable as a material for preparing the dihaloketene includes, for example, difluoroacetyl chloride, dichloroacetyl chloride, dibromoacetyl chloride, difluoroacetyl bromide, dichloroacetyl bromide and dibromoacetyl bromide. Of these, dichloroacetyl chloride is preferable.

Although the molar ratio of the dihaloacetyl halide to the isopropylcyclopentadiene is varied depending on the proportion of the 1-isomer in the isopropylcyclopentadiene, it is usually 0.1 to 10, preferably 0.5 to 5, more preferably 0.5 to 3. The molar ratio of triethylamine to the dihaloacetyl halide is 0.5 to 2, preferably 0.7 to 1.5, more preferably 0.9 to 1.1. The reason is as follows: when the molar ratio of triethylamine to the dihaloacetyl halide is lower than 0.5, the amount of unreacted dihaloacetyl halide remaining in the reaction system is increased; when the molar ratio is higher than 2, the amount of unreacted triethylamine remaining in the reaction system is increased and there is a strong tendency that the isomerization of 1-isopropylcyclopentadiene to 2-isopropylcyclopentadiene is accelerated.

The yield of the ketene adducts as products and the ratio between the adduct derived from 1-isopropylcyclopentadiene (hereinafter abbreviated as 1-isomer adduct) and the adduct derived from 2-isopropylcyclopentadiene (2-isomer adduct) among the ketene adducts vary depending on the amount of the dihaloketene prepared from the dihaloacetyl halide and triethylamine used in the above amount ranges. In general, when the amount of the dihaloketene is large, the yield of the ketene adducts is increased but the proportion of the 1-isomer adduct among the ketene adducts is decreased. When the amount of the dihaloketene is small, the yield of the ketene adducts is decreased but the proportion of the 1-isomer adduct among the ketene adducts is increased. This is because the addition of the dihaloketene to 1-isopropylcyclopentadiene proceeds in preference to that to 2-isopropylcyclopentadiene.

The reaction temperature in the second step is usually −30° C. to 50° C., preferably −30° C. to 30° C., more preferably −10° C. to 10° C. The reason is as follows: too low a reaction temperature is not practical because the progress of the reaction is slow, and too high a reaction temperature tends to causes the isomerization of unreacted 1-isopropylcyclopentadiene to 2-isopropylcyclopentadiene or the polymerization of the ketene prepared.

When the reaction in the second step is carried out in a tank reactor, it is preferably carried out with stirring. The reaction is carried out at a degree of stirring of preferably 0.1 kW or more, more preferably 0.2 kW or more, per cubic meter of the reaction solution. This is because when the degree of stirring is less than $0.1 \text{ kW/m}^3$, the ketene prepared tends to be polymerized in an increased proportion instead of being added to isopropylcyclopentadiene.

When the dihaloketene is prepared by the dehydrohalogenation of a dihaloacetyl halide, the reaction mixture is preferably diluted with a solvent because a large amount of a hydrogen halide salt of triethylamine is formed, so that stirring becomes difficult in some cases. As the solvent, any solvent may be used so long as it is inert to the dihaloacetyl halide and the dihaloketene. The solvent includes, for example, saturated hydrocarbons such as pentane, hexane, heptane, cyclohexane, petroleum ether, etc. When the isopropylcyclopentadiene obtained by the after-treatment in the first step is in the form of a solution in hexane, it can be subjected as it is to the second step.

The after-treatment of the reaction solution after completion of the second step is carried out as follows. The hydrogen halide salt of triethylamine is removed from the reaction solution by filtration, centrifugation or the like, after which the reaction solution is washed with a mineral acid such as hydrochloric acid or repeatedly washed with water. Alternatively, a mineral acid or water is added to the reaction solution to dissolve the hydrogen halide salt of triethylamine, after which the aqueous phase, the lower phase is taken out and the organic phase containing the ketene adducts is collected. The saturated hydrocarbon used as a solvent is distilled off from the obtained organic phase containing the ketene adducts. After the distilling-off of the solvent, the ketene adducts may be further purified by distillation or used as they are as starting materials in the subsequent third step.

On the other hand, the recovery of triethylamine from the aqueous phase containing the hydrogen halide salt of triethylamine, which has been removed by separation from the organic phase containing the ketene adducts in the after-treatment, is important from the viewpoint of resources saving. The aqueous phase containing the hydrogen halide salt of triethylamine is neutralized or alkalized with an inorganic base such as sodium hydroxide. In this case, if necessary, water is added so that no precipitated salt may be present. Thus, the organic phase containing triethylamine and the aqueous phase containing an inorganic salt such as sodium halide are separated from each other. The aqueous phase is removed, after which the organic phase containing triethylamine is collected and this triethylamine is purified by distillation. The purified triethylamine can be reused as a starting material in the second step.

Next, the third step is explained below. The third step is a step of producing hinokitiol by decomposing the ketene adducts obtained in the second step, in a mixed solvent containing a base.

As the mixed solvent, there are known acetic acid-potassium acetate-water systems, acetic acid-sodium acetate-water systems, and acetic acid-triethylamineacetone-water systems. It is said that the decomposition is triggered by abstraction of chlorine from the ketene adducts. The base is used as a chlorine catcher. The presence of water as a hydroxyl group source for the production of hinokitiol is indispensable. As a result of investigation by the present inventors, it was found that systems using triethylamine among the systems used in the above prior arts are preferable because the time required is short.

As a result of earnest investigation on the systems using triethylamine, the following was found. In the prior arts, the decomposition reaction is carried out by charging a mixed solvent and starting ketene adducts all at once. As a result of GPC analysis of the reaction solution by the present inventors, it was found that in this case, a large amount of high-boiling substances are produced as by-products. Moreover, it was found that the amount of the high-boiling by-products is not significantly increased in proportion to the reaction time and that the production of the high-boiling by-products is increased in the initial period during the reaction. Thus, it is preferable to add triethylamine dropwise or in small portions instead of charging a predetermined amount of triethylamine at first, because the production of the high-boiling by-products is greatly reduced, resulting in an increased yield of hinokitiol. In addition, it was found that although acetic acid is added as an essential component in the prior arts, employment of the triethylamine dropwise addition method found by the present inventors makes it possible to obtain hinokitiol in high yield without acetic acid. The yield of hinokitiol is further increased not only by the addition of acetic acid but also by the addition of at least one organic acid selected from formic acid and propionic acid.

It was also found that the reaction gives a bis-ring compound formed by attachment of a lactone ring to a 5-membered ring (hereinafter abbreviated as "lactone by-product") as a by-product in addition to the high-boiling by-products. The lactone by-product has a boiling point near that of hinokitiol, a desired product. Therefore, when the amount of the lactone by-product produced is large, the purification of hinokitiol becomes difficult. Accordingly, it is preferable to reduce the amount of the lactone by-product produced by the reaction. As to this problem, the present inventors found that the production of the lactone by-product can be greatly reduced by using tertiary butanol as a water-soluble organic solvent in place of acetone.

Although the ratio among the components used in the reaction are not particularly limited, the molar ratio of water to the starting ketene adducts is 0.1 to 30, preferably 0.5 to 20, more preferably 0.8 to 10. The molar ratio of triethylamine to the ketene adducts is 0.1 to 10, preferably 0.5 to 5, more preferably 0.8 to 3. The molar ratio of the organic acid(s) to triethylamine is 0 to 0.9, preferably 0 to 0.7, more preferably 0 to 0.5. This is because when the molar ratio of the organic acid(s) to triethylamine is more than 1, the reaction does not proceed. Although the amount of the hydrophilic organic solvent is not particularly limited, the molar ratio of the hydrophilic organic solvent to the ketene adducts ranges usually from 5 to 30.

As the reaction temperature in the third step, there is employed a temperature higher than those employed in the first step and the second step. The reaction temperature ranges usually from 50° C. to 140° C. At atmospheric pressure, the reaction is preferably carried out at the reflux temperature of the reaction system.

The reaction solution containing crude hinokitiol which has been thus obtained in the third step is properly subjected to operations such as extraction, washing, etc. In addition, purification is carried out by distillation, recrystallization or a combination of distillation and recrystallization, depending on purpose of use or a purity required of the final product.

An aqueous solution containing triethylamine hydrochloride is produced as waste water in the extraction and washing of the reaction solution containing crude hinokitiol. The triethylamine can be reused after being recovered from the waste water by the same method as in the second step.

A point to which attention should be paid in the purification of the crude hinokitiol is that hinokitiol tends to form a chelate complex with iron and hence is easily colored, namely, hinokitiol seriously corrodes the an apparatus made of iron. Therefore, as to a material for an apparatus with which hinokitiol comes into contact, it is preferable to use an apparatus made of a high-grade metal such as Hastelloy C, an apparatus made of or lined with glass, an apparatus coated with a resin such as Teflon, or an apparatus made of or coated with ceramic. For rectifying hinokitiol, a ceramic packing is preferably used.

Examples of the present invention are described below but they are not intended in any way to limit the scope of the present invention.

Conditions of gas-chromatographic analysis of the products obtained according to the present invention are described below.

1. Analysis of isopropylcyclopentadiene
Apparatus: Type GC-14A of Shimadzu Corp., Chromatopack CR-4A of Shimadzu Corp.
Column: Capillary Column DB-1 of J & W Scientific Co. (length 30 m×inside diameter 0.25 mm, liquid phase thickness 0.25 μm).
Temperature conditions: column 40° C.×5 min.→250° C. (10° C./min.). inlet 60° C., detector 250° C. (FID).
2. Analysis of the adducts and solvolysis products
Apparatus: Type GC-14A of Shimadzu Corp., Chromatopack CR-4A of Shimadzu Corp.

Column: Capillary Column DB-1 of J & W Scientific Co. (length 30 m×inside diameter 0.25 mm, liquid phase thickness 0.25 μm).

Temperature conditions: column 100° C.×2 min.→250° C. (10° C./min.). inlet 300° C., detector 300° C. (FID).

Reagents used in the examples of the present invention are as follows:

Cyclopentadiene
  Produced by pyrolyzing dicyclopentadiene (mfd. by Wako Pure Chemical Industries, Ltd.) at 160° C.
Potassium hydroxide
  85% potassium hydroxide: mfd. by Katayama Chemical Co., Ltd.
  96% potassium hydroxide: mfd. by Nippon Soda Co., Ltd.
Sodium hydroxide: mfd. by Katayama Chemical Co., Ltd.
Lithium hydroxide: mfd. by Wako Pure Chemical Industries, Ltd.
Rubidium hydroxide: mfd. by Ishidzu Pharmaceutical Co., Ltd.
Caesium hydroxide: mfd. by Kishida Chemical Co., Ltd.
Potassium ethoxide: mfd. by Aldrich.
Isopropyl bromide: mfd. by Tokyo Kasei Kogyo Co., Ltd.
Dimethyl sulfoxide: mfd. by Wako Pure Chemical Industries, Ltd.; special grade.
Acetonitrile: mfd. by Wako Pure Chemical Industries, Ltd.; special grade.
Dimethylformamide: mfd. by Wako Pure Chemical Industries, Ltd.; special grade.
1,3-dimethyl-2-imidazolidinone:
  mfd. by Wako Pure Chemical Industries, Ltd.; special grade.
n-Hexane: mfd. by Wako Pure Chemical Industries, Ltd.; special grade.
n-Heptane: mfd. by Wako Pure Chemical Industries, Ltd.; special grade.
n-Octane: mfd. by Wako Pure Chemical Industries, Ltd.; special grade.
Dichloroacetyl chloride: mfd. by Tokyo Kasei Kogyo Co., Ltd.
Triethylamine: mfd. by Wako Pure Chemical Industries, Ltd.; special grade.
Acetic acid: mfd. by Katayama Chemical Co., Ltd.; special grade.
Acetone: mfd. by Katayama Chemical Co., Ltd.; first grade.
Tertiary butanol: mfd. by Wako Pure Chemical Industries, Ltd.; special grade.
Tetrahydrofuran: mfd. by Wako Pure Chemical Industries, Ltd.; special grade.
Ethanol: mfd. by Wako Pure Chemical Industries, Ltd.; 99.8%.

EXAMPLE 1

To 281.3 g (3.6 mols) of dimethyl sulfoxide were added 49.3 g (0.72 mol) of cyclopentadiene (purity: 96.3%) and 39.6 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

The molar ratio of water to cyclopentadienylpotassium was 1.6.

To the cyclopentadienylpotassium solution was added 140.0 g of n-hexane, after which 147.6 g (1.2 mols) of isopropyl bromide was added dropwise with stirring over a period of 50 minutes while maintaining the solution temperature at 5° C. After completion of the dropwise addition, 1N hydrochloric acid and n-hexane were added and then the organic layer was separated to obtain 309 g of a n-hexane solution containing isopropylcyclopentadiene.

The n-hexane solution was analyzed by a gas chromatography to find that the yield of isopropylcyclopentadiene was 95.9% (0.58 mol) and that the ratio among its isomers was as follows: 1-isomer:5-isomer:2-isomer=27.0:65.1:7.9.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=91.0:1.1:7.9.

To the n-hexane solution was added 294 g of n-hexane to obtain 603 g of a n-hexane solution containing 62.3 g (0.58 mol) of isopropylcyclopentadiene. To this n-hexane solution was added 89.1 g (0.60 mol) of dichloroacetyl chloride, after which 64.1 g (0.63 mol) of triethylamine was added dropwise with stirring over a period of 2 hours while maintaining the solution temperature at 0° C. The degree of stirring was 0.3 kW/m$^3$. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 82% (0.47 mol).

The n-hexane was distilled off from the n-hexane solution containing the ketene adducts, and the residue was distilled under reduced pressure to obtain 95.7 g (0.42 mol) of a distillate containing the ketene adducts (purity: 95%). The ketene adducts were analyzed by a gas chromatography to find that the ratio among the ketene adducts derived from 1-isomer, 5-isomer and 2-isomer, respectively, of isopropylcyclopentadiene was 99.8:0:0.2.

A mixed solvent consisting of 25 g of acetic acid, 314 g of acetone and 52 g of water was added to the distillate containing the ketene adducts, and 105 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the adducts disappeared and that hinokitiol was obtained in 76% yield (0.32 mol).

EXAMPLE 2

The process of Example 1 was repeated, except that in the isopropylation step, the molar ratio of dimethyl sulfoxide to cyclopentadienylpotassium was changed and that after completion of the dropwise addition of isopropyl bromide, the lower layer was taken out without adding 1N hydrochloric acid and hexane.

To 233.7 g (3.0 mols) of dimethyl sulfoxide were added 49.8 g (0.72 mol) of cyclopentadiene (purity: 95.1%) and 39.5 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 5.0.

To the cyclopentadienylpotassium solution was added 140.5 g of n-hexane, after which 147.4 g (1.2 mols) of isopropyl bromide was added dropwise over a period of 45 minutes while maintaining the solution temperature at 5° C. After completion of the dropwise addition, the organic layer was separated to obtain 270 g of a n-hexane solution containing isopropylcyclopentadiene.

The n-hexane solution was analyzed by a gas chromatography to find that the yield of isopropylcyclopentadiene was 93.8% (0.56 mol) and that the ratio among its isomers was as follows: 1-isomer:5-isomer:2-isomer=22.2:65.0:12.8.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=86.2:1.0:12.8.

To the n-hexane solution was added 317 g of n-hexane to obtain 587 g of a n-hexane solution containing 60.7 g (0.56 mol) of isopropylcyclopentadiene. To this n-hexane solution was added 86.8 g (0.59 mol) of dichloroacetyl chloride, after which 62.4 g (0.62 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 79% (0.44 mol).

The n-hexane was distilled off from the n-hexane solution containing the ketene adducts, and the residue was distilled under reduced pressure to obtain 91.8 g (0.39 mol) of a distillate containing the ketene adducts (purity: 93%). The distillate containing the ketene adducts was analyzed by a gas chromatography to find that the ratio among the ketene adducts derived from 1-isomer, 5-isomer and 2-isomer, respectively, of isopropylcyclopentadiene was 98.0:0:2.0.

A mixed solvent consisting of 23 g of acetic acid, 294 g of acetone and 49 g of water was added to the distillate containing the ketene adducts, and 99 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the adducts disappeared and that hinokitiol was obtained in 73% yield (0.28 mol).

EXAMPLE 3

The process of Example 1 was repeated except for carrying out isopropylation at a changed molar ratio of dimethyl sulfoxide to cyclopentadienylpotassium.

To 140.7 g (1.8 mols) of dimethyl sulfoxide were added 49.4 g (0.71 mol) of cyclopentadiene (purity: 95.1%) and 39.4 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 3.0.

To the cyclopentadienylpotassium solution was added 140.9 g of n-hexane, after which 147.4 g (1.2 mols) of isopropyl bromide was added dropwise over a period of 50 minutes while maintaining the solution temperature at 5° C. After completion of the dropwise addition, 1N hydrochloric acid and n-hexane were added and then the organic layer was separated to obtain 307 g of a n-hexane solution containing isopropylcyclopentadiene.

The n-hexane solution was analyzed by a gas chromatography to find that the yield of isopropylcyclopentadiene was 52.8% (0.31 mol) and that the ratio among its isomers was as follows: 1-isomer:5-isomer:2-isomer=33.7:31.6:34.7.

The 5-isomer was isomerized to 1-isomer by allowing the n-hexane solution containing isopropylcyclopentadiene, to stand at 20° C. for 6 hours. The ratio among the isomers after the isomerization was as follows: 1-isomer:5-isomer:2-isomer=64.3:1.0:34.7.

To the n-hexane solution was added 23 g of n-hexane to obtain 330 g of a n-hexane solution containing 34.1 g (0.31 mol) of isopropylcyclopentadiene. To this n-hexane solution was added 48.75 g (0.33 mol) of dichloroacetyl chloride, after which 35.0 g (0.35 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 70% (0.22 mol).

The n-hexane was distilled off from the n-hexane solution containing the ketene adducts, and the residue was distilled under reduced pressure to obtain 45.2 g (0.19 mol) of a distillate containing the ketene adducts (purity: 94%). The distillate containing the ketene adducts was analyzed by a gas chromatography to find that the ratio among the ketene adducts derived from 1-isomer, 5-isomer and 2-isomer, respectively, of isopropylcyclopentadiene was 82.7:0:17.3.

A mixed solvent consisting of 12 g of acetic acid, 147 g of acetone and 24 g of water was added to the distillate containing the ketene adducts, and 49 g of triethylamine was added dropwise over a period of 2 hours while maintaining the solution temperature at 60° C. Then, the resulting mixture was heated at 60° C for another 5 hours. After completion of the reaction, analysis by a gaschromatography revealed that peaks due to the ketene adducts disappeared and that hinokitiol was obtained in 60% yield (0.12 mol).

EXAMPLE 4

The process of Example 1 was repeated except for carrying out isopropylation by adding a cyclopentadienylpotassium solution dropwise.

To 281.3 g (3.6 mols) of dimethyl sulfoxide were added 49.3 g (0.71 mol) of cyclopentadiene (purity: 95.7%) and 39.6 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

To 147.6 g (1.2 mols) of isopropyl bromide was added 140.0 g of n-hexane, after which the above-mentioned cyclopentadienylpotassium solution was added dropwise over a period of 70 minutes while maintaining the solution temperature at 10° C. After completion of the dropwise addition, 1N hydrochloric acid and n-hexane were added and then the organic layer was separated to obtain 309 g of a n-hexane solution containing isopropylcyclopentadiene.

The n-hexane solution was analyzed by a gas chromatography to find that the yield of isopropylcyclopentadiene was 94.9% (0.57 mol) and that the ratio among its isomers was as follows: 1-isomer:5-isomer:2-isomer=40.9:50.5:8.6.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=90.4:1.0:8.6.

To the n-hexane solution was added 287 g of n-hexane to obtain 596 g of a n-hexane solution containing 61.6 g (0.57 mol) of isopropylcyclopentadiene. To this n-hexane solution was added 88.1 g (0.60 mol) of dichloroacetyl chloride, after which 63.4 g (0.63 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 81% (0.46 mol).

The n-hexane was distilled off from the n-hexane solution containing the ketene adducts, and the residue was distilled under reduced pressure to obtain 96.7 g (0.41 mol) of a distillate containing the ketene adducts (purity: 92%). The distillate containing the ketene adducts was analyzed by a gas chromatography to find that the ratioamong the ketene adducts derived from 1-isomer, 5-isomer and 2-isomer, respectively, of isopropylcyclopentadiene was 99.7:0:0.3.

A mixed solvent consisting of 24 g of acetic acid, 306 g of acetone and 51 g of water was added to the distillate containing the ketene adducts, and 103 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 74% yield (0.30 mol).

EXAMPLE 5

The process of Example 1 was repeated except for carrying out isopropylation at a changed molar ratio of dimethyl sulfoxide to cyclopentadienylpotassium without adding an aliphatic hydrocarbon.

To 469.3 g (6.0 mols) of dimethyl sulfoxide were added 42.1 g (0.60 mol) of cyclopentadiene (purity: 94.5%) and 33.2 g (0.50 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 11.9.

To the cyclopentadienylpotassium solution wasadded dropwise 124.1 g (1.0 mol) of isopropyl bromide over a period of 55 minutes while maintaining the solution temperature at 5° C. After completion of the dropwise addition, 1N hydrochloric acid and n-hexane were added and then the organic layer was separated to obtain 259 g of a n-hexane solution containing isopropylcyclopentadiene.

The n-hexane solution was analyzed by a gas chromatography to find that the yield of isopropylcyclopentadiene was 93.6% (0.47 mol) and that the ratio among its isomers was as follows: 1-isomer:5-isomer:2-isomer=42.5:42.8:14.7.

The 5-isomer was isomerized to 1-isomer by allowing the n-hexane solution containing isopropylcyclopentadiene, to stand at 20° C. for 6 hours. The ratio among the isomers after the isomerization was as follows: 1-isomer:5-isomer:2-isomer=84.1:1.2:14.7.

To the n-hexane solution was added 234 g ofn-hexane to obtain 493 g of a n-hexane solution containing 50.9 g (0.47 mol) of isopropylcyclopentadiene. To this n-hexane solution was added 72.9 g (0.49 mol) of dichloroacetyl chloride, after which 52.4 g (0.52 mol) oftriethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 73% (0.34 mol).

The n-hexane was distilled off from the n-hexane solution containing the ketene adducts, and the residue was distilled under reduced pressure to obtain 69.7 g (0.30 mol) of a distillate containing the ketene adducts (purity: 95%). The distillate containing the ketene adducts was analyzed by a gas chromatography to find that the ratio among the ketene adducts derived from 1-isomer, 5-isomer and 2-isomer, respectively, of isopropylcyclopentadiene was 97.5:0:2.5.

A mixed solvent consisting of 18 g of acetic acid, 228 g of acetone and 38 g of water was added to the distillate containing the ketene adducts, and 77 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 71% yield (0.21 mol).

EXAMPLE 6

The process of Example 1 was repeated except for carrying out isopropylation without adding an aliphatic hydrocarbon.

To 273.5 g (3.5 mols) of dimethyl sulfoxide were added 49.4 g (0.71 mol) of cyclopentadiene (purity: 94.7%) and 38.5 g (0.58 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

To the cyclopentadienylpotassium solution was added dropwise 143.3 g (1.2 mols) of isopropyl bromide over a period of 50 minutes while maintaining the solution temperature at 5° C. After completion of the dropwise addition, 1N hydrochloric acid and n-hexane were added and then the organic layer was separated to obtain 300 g of a n-hexane solution containing isopropylcyclopentadiene.

The n-hexane solution was analyzed by a gas chromatography to find that the yield of isopropylcyclopentadiene was 94.7% (0.55 mol) and that the ratio among its isomers was as follows: 1-isomer:5-isomer:2-isomer=36.2:50.8:13.0.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=85.6:1.4:13.0.

To the n-hexane solution was added 278 g of n-hexane to obtain 578 g of a n-hexane solution containing 59.7 g (0.55 mol) of isopropylcyclopentadiene. To this n-hexane solution was added 85.5 g (0.58 mol) of dichloroacetyl chloride, after which 61.5 g (0.61 mol) oftriethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 73% (0.40 mol).

The n-hexane was distilled off from the n-hexane solution containing the ketene adducts, and the residue was distilled under reduced pressure to obtain 82.7 g (0.36 mol) of a distillate containing the ketene adducts (purity: 95%). The distillate containing the ketene adducts was analyzed by a gas chromatography to find that the ratio among the ketene adducts derived from 1-isomer, 5-isomer and 2-isomer, respectively, of isopropylcyclopentadiene was 97.6:0:2.4.

A mixed solvent consisting of 21 g of acetic acid, 268 g of acetone and 45 g of water was added to the distillate containing the ketene adducts, and 90 g of triethylamine was added dropwise over a period of 2 hours while maintaining the solution temperature at 60° C. Then, the resulting mixture was heated at 60° C. for another 5 hours. After completion of the reaction, analysis by a gaschromatography revealed that peaks due to the ketene adducts disappeared and that hinokitiol was obtained in 72% yield (0.26 mol).

EXAMPLE 7

The process of Example 1 was repeated except for carrying out isopropylation at a changed molar ratio of dimethyl sulfoxide to cyclopentadienylpotassium without adding an aliphatic hydrocarbon.

To 213.7 g (2.7 mols) of dimethyl sulfoxide were added 75.1 g (1.07 mols) of cyclopentadiene (purity: 94.5%) and 59.2 g (0.90 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 3.0.

To the cyclopentadienylpotassium solution was added dropwise 220.7 g (1.8 mols) of isopropyl bromide over a period of 80 minutes while maintaining the solution temperature at 5° C. After completion of the dropwise addition, 1N hydrochloric acid and n-hexane were added and then the organic layer was separated to obtain 462 g of a n-hexane solution containing isopropylcyclopentadiene.

The n-hexane solution was analyzed by a gas chromatography to find that the yield of isopropylcyclopentadiene was 99.0% (0.89 mol) and that the ratio among its isomers was as follows: 1-isomer:5-isomer:2-isomer=41.6:28.7:29.7.

The 5-isomer was isomerized to 1-isomer by allowing the n-hexane solution containing isopropylcyclopentadiene, to stand at 20° C. for 5 hours. The ratio among the isomers after the isomerization was as follows: 1-isomer:5-isomer:2-isomer=69.2:1.1:29.7.

To the n-hexane solution was added 468 g of n-hexane to obtain 930 g of a n-hexane solution containing 96.0 g (0.89 mol) of isopropylcyclopentadiene. To this n-hexane solution was added 137.4 g (0.93 mol) of dichloroacetyl chloride, after which 98.8 g (0.98 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution ontaining ketene adducts.

The n-hexane solution containing ketene adducts as analyzed by a gas chromatography to find that the yield of the ketene adducts was 71% (0.63 mol).

The n-hexane was distilled off from the n-hexane solution containing the ketene adducts, and the residue was distilled under reduced pressure to obtain 132.0 g (0.56 mol) of a distillate containing the ketene adducts (purity: 92%). The distillate containing the ketene adducts was analyzed by a gas chromatography to find that the ratio among the ketene adducts derived from 1-isomer, 5-isomer and 2-isomer, respectively, of isopropylcyclopentadiene was 87.7:0:12.3.

A mixed solvent consisting of 33 g of acetic acid, 419 g of acetone and 70 g of water was added to the distillate containing the ketene adducts, and 140 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 65% yield (0.36 mol).

EXAMPLE 8

The process of Example 1 was repeated except for carrying out isopropylation by adding a cyclopentadienylpotassium solution dropwise but not an aliphatic hydrocarbon.

To 1,342.3 g (17.2 mols) of dimethyl sulfoxide were added 128.5 g (1.72 mols) of cyclopentadiene (purity: 8.2%) and 91.5 g (1.43 mols) of potassium hydroxide (purity: 88%), and the resulting mixture was stirred for 1.5 hours in a nitrogen stream at room temperature to obtain a cyclopentadienylpotassium solution. The molar ratio of dimethyl sulfoxide to cyclopentadienylpotassium was 12.0.

To 352.0 g (2.9 mols) of isopropyl bromide was added dropwise the above-mentioned cyclopentadienylpotassium solution over a period of 170 minutes while maintaining the solution temperature at 10° C. Aftercompletion of the dropwise addition, 1N hydrochloric acid and n-hexane were added and then the organic layer was separated to obtain 709 g of a n-hexane solution containing isopropylcyclopentadiene.

The n-hexane solution was analyzed by a gas chromatography to find that the yield of isopropylcyclopentadiene was 93.0% (1.33 mols) and that the ratio among its isomers was as follows: 1-isomer:5-isomer:2-isomer=49.8:43.4:6.8.

The 5-isomer was isomerized to 1-isomer by allowing the n-hexane solution containing isopropylcyclopentadiene, to stand at 20° C. for 5 hours. The ratio among the isomers after the isomerization was as follows: 1-isomer:5-isomer:2-isomer=92.0:1.2:6.8.

To the n-hexane solution was added 681 g of n-hexane to obtain 1,390 g of a n-hexane solution containing 143.6 g (1.33 mols) of isopropylcyclopentadiene. To this n-hexane solution was added 205.4 g (1.39 mols) of dichloroacetyl chloride, after which 147.7 g (1.46 mols) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 82.8% (1.10 mols).

The n-hexane was distilled off from the n-hexane solution containing the ketene adducts, and the residue was distilled under reduced pressure to obtain 227.7 g (0.97 mol) of a distillate containing the ketene adducts (purity: 93%). The distillate containing the ketene adducts was analyzed by a gas chromatography to find that the ratio among the ketene adducts derived from 1-isomer, 5-isomer and 2-isomer, respectively, of isopropylcyclopentadiene was 99.8:0.1:0.1.

A mixed solvent consisting of 58 g of acetic acid, 730 g of acetone and 122 g of water was added to the distillate containing the ketene adducts, and 245 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 76% yield (0.73 mol).

EXAMPLE 9

The process of Example 1 was repeated except for carrying out isopropylation by adding a cyclopentadienylpotassium solution dropwise but not an aliphatic hydrocarbon.

To 180.3 g (2.3 mols) of dimethyl sulfoxide were added 19.6 g (0.28 mol) of cyclopentadiene (purity: 94.0%) and 14.7 g (0.23 mol) of potassium hydroxide (purity: 87%), and the resulting mixture was stirred for 1.5 hours in a nitrogen stream at room temperature to obtain a cyclopentadienylpotassium solution. The molar ratio of dimethyl sulfoxide to cyclopentadienylpotassium was 10.2.

To 49.6 g (0.4 mol) of isopropyl bromide was added dropwise the above-mentioned cyclopentadienylpotassium solution over a period of 120 minutes while maintaining the solution temperature at 0° C. After completion of the dropwise addition, 1N hydrochloric acid and n-hexane were added and then the organic layer was separated to obtain 117 g of a n-hexane solution containing isopropylcyclopentadiene.

The n-hexane solution was analyzed by a gas chromatography to find that the yield of isopropylcyclopentadiene was 93.7% (0.21 mol) and that the ratio among its isomers was as follows: 1-isomer:5-isomer:2-isomer=40.1:53.2:6.7.

The 5-isomer was isomerized to 1-isomer by allowing the n-hexane solution containing isopropylcyclopentadiene, to stand at 20° C. for 7 hours. The ratio among the isomers after the isomerization was as follows:1-isomer:5-isomer:2-isomer=92.7:0.6:6.7.

To the n-hexane solution was added 106 g of n-hexane to obtain 223 g of a n-hexane solution containing 23.0 g (0.21 mol) of isopropylcyclopentadiene. To this n-hexane solution was added 32.9 g (0.22 mol) of dichloroacetyl chloride, after which 23.6 g (0.23 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 82.0% (0.17 mol).

The n-hexane was distilled off from the n-hexane solution containing the ketene adducts, and the residue was distilled under reduced pressure to obtain 35.7 g (0.15 mol) of a distillate containing the ketene adducts (purity: 94%). The distillate containing the ketene adducts was analyzed by a gas chromatography to find that the ratio among the ketene adducts derived from 1-isomer, 5-isomer and 2-isomer, respectively, of isopropylcyclopentadiene was 99.8:0.1:0.1.

A mixed solvent consisting of 9 g of acetic acid, 116 g of acetone and 19 g of water was added to the distillate containing the ketene adducts, and 39 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 75% yield (0.11 mol).

EXAMPLE 10

The process of Example 1 was repeated except for carrying out isopropylation by adding a cyclopentadienylpotassium solution dropwise but not an aliphatic hydrocarbon.

To 330.0 g (4.2 mols) of dimethyl sulfoxide were added 35.0 g (0.50 mol) of cyclopentadiene (purity: 95.0%) and 31.7 g (0.48 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 8.8.

To 106.4 g (0.9 mol) of isopropyl bromide was added dropwise the above-mentioned cyclopentadienylpotassium solution over a period of 160 minutes while maintaining the solution temperature at 5° C. After completion of the dropwise addition, 1N hydrochloric acid and n-hexane were added and then the organic layer was separated to obtain 247 g of a n-hexane solution containing isopropylcyclopentadiene.

The n-hexane solution was analyzed by a gas chromatography to find that the yield of isopropylcyclopentadiene was 99.0% (0.47 mol) and that the ratio among its isomers was as follows: 1-isomer:5-isomer:2-isomer=43.9:18.8:37.3.

The 5-isomer was isomerized to 1-isomer by allowing the n-hexane solution containing isopropylcyclopentadiene, to stand at 20° C. for 20 hours. The ratio among the isomers after the isomerization was as follows: 1-isomer:5-isomer:2-isomer=61.1:0.2:38.7.

To the n-hexane solution was added 250 g of n-hexane to obtain 497 g of a n-hexane solution containing 51.3 g (0.47 mol) of isopropylcyclopentadiene. To this n-hexane solution was added 73.4 g (0.50 mol) of dichloroacetyl chloride, after which 52.8 g (0.52 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 70% (0.33 mol).

The n-hexane was distilled off from the n-hexane solution containing the ketene adducts, and the residue was distilled under reduced pressure to obtain 67.4 g (0.29 mol) of a distillate containing the ketene adducts (purity: 95%). The distillate containing the ketene adducts was analyzed by a gas chromatography to find that the ratio among the ketene adducts derived from 1-isomer, 5-isomer and 2-isomer, respectively, of isopropylcyclopentadiene was 78.4:0:21.6.

A mixed solvent consisting of 18 g of acetic acid, 221 g of acetone and 37 g of water was added to the distillate containing the ketene adducts, and 74 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 52% yield (0.15 mol).

EXAMPLE 11

The process of Example 1 was repeated except for carrying out the isopropylation step at 20° C.

To 281.4 g (3.6 mols) of dimethyl sulfoxide were added 49.4 g (0.71 mol) of cyclopentadiene (purity: 95.12%)

and 39.4 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

To the cyclopentadienylpotassium solution was added 140.0 g of n-hexane, after which 147.5 g (1.2 mols) of isopropyl bromide was added dropwise over a period of 50 minutes while maintaining the solution temperature at 20° C. After completion of the dropwise addition, 1N hydrochloric acid and n-hexane were added and then the organic layer was separated to obtain 308 g of a n-hexane solution containing isopropylcyclopentadiene.

The n-hexane solution was analyzed by a gas chromatography to find that the yield of isopropylcyclopentadiene was 93.1% (0.56 mol) and that the ratio among 15 its isomers was as follows: 1-isomer:5-isomer:2-isomer= 39.0:46.9:14.1.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=84.8:1.1:14.1.

To the n-hexane solution was added 275 g of n-hexane to obtain 583 g of a n-hexane solution containing 60.2 g (0.56 mol) of isopropylcyclopentadiene. To this n-hexane solution was added 86.1 g (0.58 mol) of dichloroacetyl chloride, after which 61.9 g (0.61 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 78% (0.44 mol).

The n-hexane was distilled off from the n-hexane solution containing the ketene adducts, and the residue was distilled under reduced pressure to obtain 89.0 g (0.38 mol) of a distillate containing the ketene adducts (purity: 94%). The ketene adducts were analyzed by a gas chromatography to find that the ratio among the ketene adducts derived from 1-isomer, 5-isomer and 2-isomer, respectively, of isopropylcyclopentadiene was 98.0:0:2.0.

A mixed solvent consisting of 23 g of acetic acid, 288 g of acetone and 48 g of water was added to the distillate containing the ketene adducts, and 97 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 73% yield (0.28 mol).

EXAMPLE 12

The process of Example 1 was repeated except for carrying out the isopropylation step at 30° C.

To 281.2 g (3.6 mols) of dimethyl sulfoxide were added 49.4 g (0.71 mol) of cyclopentadiene (purity: 95.12%) and 39.6 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

To the cyclopentadienylpotassium solution was added 140.0 g of n-hexane, after which 147.4 g (1.2 mols) of isopropyl bromide was added dropwise over a period of 50 minutes while maintaining the solution temperature at 30° C.

After completion of the dropwise addition, 1N hydrochloric acid and n-hexane were added and then the organic layer was separated to obtain 309 g of a n-hexane solution containing isopropylcyclopentadiene.

The n-hexane solution was analyzed by a gas chromatography to find that the yield of isopropylcyclopentadiene was 91.9% (0.55 mol) and that the ratio among its isomers was as follows: 1-isomer:5-isomer:2-isomer=49.5:13.9:36.6.

The 5-isomer was isomerized to 1-isomer by allowing the n-hexane solution containing isopropylcyclopentadiene, to stand at 20° C. for 5 hours. The ratio among the isomers after the isomerization was as follows: 1-isomer:5-isomer:2-isomer=62.4:1.0:36.6.

To the n-hexane solution was added 268 g of n-hexane to obtain 577 g of a n-hexane solution containing 59.6 g (0.55 mol) of isopropylcyclopentadiene. To this n-hexane solution was added 85.2 g (0.58 mol) of dichloroacetyl chloride, after which 61.3 g (0.61 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 70% (0.39 mol).

The n-hexane was distilled off from the n-hexane solution containing the ketene adducts, and the residue was distilled under reduced pressure to obtain 78.2 g (0.34 mol) of a distillate containing the ketene adducts (purity: 95%). The ketene adducts were analyzed by a gas chromatography to find that the ratio among the ketene adducts derived from 1-isomer, 5-isomer and 2-isomer, respectively, of isopropylcyclopentadiene was 80.2:0:19.8.

A mixed solvent consisting of 20 g of acetic acid, 256 g of acetone and 43 g of water was added to the distillate containing the ketene adducts, and 86 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 58% yield (0.20 mol).

EXAMPLE 13

There is described below a case where the water content of a cyclopentadienylpotassium solution was reduced by using potassium hydroxide having a low water content (except for this reduction, the conditions employed in this example were the same as in Example 1).

To 281.3 g (3.6 mols) of dimethyl sulfoxide were added 50.3 g (0.73 mol) of cyclopentadiene (purity: 96.3%) and 35.1 g (0.60 mol) of potassium hydroxide (purity: 96%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0. The molar ratio of water to cyclopentadienylpotassium was 1.1.

To the cyclopentadienylpotassium solution was added 140.0 g of n-hexane, after which 147.6 g (1.2 mols) of isopropyl bromide was added dropwise over a period of 50 minutes while maintaining the solution temperature at 5° C. After completion of the dropwise addition, 1N hydrochloric acid and n-hexane were added and then the organic layer was separated to obtain 309 g of a n-hexane solution containing isopropylcyclopentadiene.

The n-hexane solution was analyzed by a gas chromatography to find that the yield of isopropylcyclopentadiene was 90.0% (0.54 mol) and that the ratio among its isomers was as follows: 1-isomer:5-isomer:2-isomer=19.8:73.4:6.8.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=92.2:1.0:6.8.

To the n-hexane solution was added 256 g of n-hexane to obtain 565 g of a n-hexane solution containing 58.4 g (0.54 mol) of isopropylcyclopentadiene. To this n-hexane solution was added 83.6 g (0.57 mol) of dichloroacetyl chloride, after which 60.1 g (0.59 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 82% (0.44 mol).

The n-hexane was distilled off from the n-hexane solution containing the ketene adducts, and the residue was distilled under reduced pressure to obtain 92.8 g (0.39 mol) of a distillate containing the ketene adducts (purity: 92%). The ketene adducts were analyzed by a gas chromatography to find that the ratio among the ketene adducts derived from 1-isomer, 5-isomer and 2-isomer, respectively, of isopropylcyclopentadiene was 99.8:0:0.2.

A mixed solvent consisting of 23 g of acetic acid, 294 g of acetone and 49 g of water was added to the distillate containing the ketene adducts, and 99 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 74% yield (0.29 mol).

EXAMPLE 14

There is described below a case where cyclopentadienylpotassium was prepared by using dimethyl sulfoxide with a high water content recovered from the isopropylation step (except for this preparation, the conditions employed in this example were the same as in Example 1).

To 296.0 g (3.6 mols) of dimethyl sulfoxide (water content: 5%) were added 49.0 g (0.71 mol) of cyclopentadiene (purity: 96.3%) and 39.1 g (0.59 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.1. The molar ratio of water to cyclopentadienylpotassium was 2.9.

To the cyclopentadienylpotassium solution was added 140.0 g of n-hexane, after which 148.0 g (1.2 mols) of isopropyl bromide was added dropwise over a period of 50 minutes while maintaining the solution temperature at 5° C. After completion of the dropwise addition, 1N hydrochloric acid and n-hexane were added and then the organic layer was separated to obtain 305 g of a n-hexane solution containing isopropylcyclopentadiene.

The n-hexane solution was analyzed by a gas chromatography to find that the yield of isopropylcyclopentadiene was 89.0% (0.53 mol) and that the ratio among its isomers was as follows: 1-isomer:5-isomer:2-isomer=45.0:35.0:20.0.

The 5-isomer was isomerized to 1-isomer by allowing the n-hexane solution containing isopropylcyclopentadiene, to stand at 20° C. for 5 hours. The ratio among the isomers after the isomerization was as follows: 1-isomer:5-isomer:2-isomer=78.9:1.1:20.0.

To the n-hexane solution was added 247 g of n-hexane to obtain 552 g of a n-hexane solution containing 57.0 g (0.53 mol) of isopropylcyclopentadiene. To this n-hexane solution was added 81.6 g (0.55 mol) of dichloroacetyl chloride, after which 58.7 g (0.58 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 72% (0.38 mol).

The n-hexane was distilled off from the n-hexane solution containing the ketene adducts, and the residue was distilled under reduced pressure to obtain 78.6 g (0.33 mol) of a distillate containing the ketene adducts (purity: 93%). The ketene adducts were analyzed by a gas chromatography to find that the ratio among the ketene adducts derived from 1-isomer, 5-isomer and 2-isomer, respectively, of isopropylcyclopentadiene was 97.5:0:2.5.

A mixed solvent consisting of 20 g of acetic acid, 252 g of acetone and 42 g of water was added to the distillate containing the ketene adducts, and 84 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 71% yield (0.24 mol).

EXAMPLE 15

The process of Example 1 was repeated except for using sodium hydroxide in place of potassium hydroxide in the preparation of cyclopentadienyl metal.

To 281.3 g (3.6 mols) of dimethyl sulfoxide were added 49.4 g (0.72 mol) of cyclopentadiene (purity: 96.0%) and 25.0 g (0.60 mol) of sodium hydroxide (purity: 96%), and the resulting mixture was stirred for 1.5 hours in a nitrogen stream at room temperature to obtain a cyclopentadienylsodium solution. The molar ratio of dimethyl sulfoxide to cyclopentadienylsodium was 6.0.

To the cyclopentadienylsodium solution was added 140.0 g of n-hexane, after which 148.0 g (1.2 mols) of isopropyl bromide was added dropwise over a period of 50 minutes while maintaining the solution temperature at 5° C. After completion of the dropwise addition, 1N hydrochloric acid and n-hexane were added and then the organic layer was separated to obtain 309 g of a n-hexane solution containing isopropylcyclopentadiene.

The n-hexane solution was analyzed by a gas chromatography to find that the yield of isopropylcyclopentadiene was 51.0% (0.31 mol) and that the ratio among its isomers was as follows: 1-isomer:5-isomer:2-isomer=19.9:73.4:6.7.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=92.2:1.1:6.7.

To the n-hexane solution was added 11 g of n-hexane to obtain 320 g of a n-hexane solution containing 10.7 g (0.31 mol) of isopropylcyclopentadiene. To this n-hexane solution was added 47.3 g (0.32 mol) of dichloroacetyl chloride, after which 34.0 g (0.034 mol) of riethylamine was added dropwise over a period of 2 hours hile maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 82% (0.25 mol).

The n-hexane was distilled off from the n-hexane solution containing the ketene adducts, and the residue was distilled under reduced pressure to obtain 52.5 g (0.22 mol) of a distillate containing the ketene adducts (purity: 92%). The ketene adducts were analyzed by a gas chromatography to find that the ratio among the ketene adducts derived from 1-isomer, 5-isomer and 2-isomer, respectively, of isopropylcyclopentadiene was 99.8:0:0.2.

A mixed solvent consisting of 13 g of acetic acid, 166 g of acetone and 28 g of water was added to the distillate containing the ketene adducts, and 56 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 73% yield (0.16 mol).

EXAMPLE 16

The process of Example 1 was repeated except for using n-heptane in place of n-hexane in the isopropylation step.

To 281.3 g (3.6 mols) of dimethyl sulfoxide were added 49.7 g (0.72 mol) of cyclopentadiene (purity: 95.74%) and 39.6 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

To the cyclopentadienylpotassium solution was added 142.1 g of n-heptane, after which 147.6 g (1.2 mols) of isopropyl bromide was added dropwise over a period of 70 minutes while maintaining the solution temperature at 5° C. After completion of the dropwise addition, 1N hydrochloric acid and n-hexane were added and then the organic layer was separated to obtain 309 g of a n-hexane solution containing isopropylcyclopentadiene.

The n-hexane solution was analyzed by a gas chromatography to find that the yield of isopropylcyclopentadiene was 90.4% (0.54 mol) and that the ratio amongits isomers was as follows: 1-isomer:5-isomer:2-isomer=31.3:61.2:7.5.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=91.5:1.0:7.5.

To the n-hexane solution was added 259 g of n-hexane to obtain 568 g of a n-hexane solution containing 58.7 g (0.54 mol) of isopropylcyclopentadiene. To this n-hexane solution was added 84.0 g (0.57 mol) of dichloroacetyl chloride, after which 60.4 g (0.60 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 82% (0.44 mol).

The n-hexane was distilled off from the n-hexane solution containing the ketene adducts, and the residue was distilled under reduced pressure to obtain 91.2 g (0.39 mol) of a distillate containing the ketene adducts (purity: 94%). The ketene adducts were analyzed by a gas chromatography to find that the ratio among the ketene adducts derived from 1-isomer, 5-isomer and 2-isomer, respectively, of isopropylcyclopentadiene was 99.7:0:0.3.

A mixed solvent consisting of 24 g of acetic acid, 296 g of acetone and 49 g of water was added to the distillate containing the ketene adducts, and 99 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 73% yield (0.29 mol).

EXAMPLE 17

The process of Example 1 was repeated except for using n-octane in place of n-hexane in the isopropylation step.

To 281.4 g (3.6 mols) of dimethyl sulfoxide were added 49.3 g (0.71 mol) of cyclopentadiene (purity: 95.74%) and 39.7 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

To the cyclopentadienylpotassium solution was added 139.1 g of n-octane, after which 147.6 g (1.2 mols) of isopropyl bromide was added dropwise over a period of 50 minutes while maintaining the solution temperature at 5° C. After completion of the dropwise addition, 1N hydrochloric acid and n-hexane were added and then the organic layer was separated to obtain 310 g of a n-hexane solution containing isopropylcyclopentadiene.

The n-hexane solution was analyzed by a gas chromatography to find that the yield of isopropylcyclopentadiene was 78.0% (0.47 mol) and that the ratio among its isomers was as follows: 1-isomer:5-isomer:2-isomer=49.1:43.1:7.8.

The 5-isomer was isomerized to 1-isomer by allowing the n-hexane solution containing isopropylcyclopentadiene, to stand at 20° C. for 6. hours. The ratio among the isomers after the isomerization was as follows: 1-isomer:5-isomer:2-isomer=91.2:1.0:7.8.

To the n-hexane solution was added 181 g of n-hexane to obtain 491 g of a n-hexane solution containing 50.7 g (0.47 mol) of isopropylcyclopentadiene. To this n-hexane solution was added 72.6 g (0.49 mol) of dichloroacetyl chloride, after which 52.2 g (0.52 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 82% (0.39 mol).

The n-hexane was distilled off from the n-hexane solution containing the ketene adducts, and the residue was distilled under reduced pressure to obtain 78.1 g (0.34 mol) of a distillate containing the ketene adducts (purity: 95%). The ketene adducts were analyzed by a gas chromatography to find that the ratio among the ketene adducts derived from 1-isomer, 5-isomer and 2-isomer, respectively, of isopropylcyclopentadiene was 99.5:0:0.5.

A mixed solvent consisting of 20 g of acetic acid, 256 g of acetone and 43 g of water was added to the distillate containing the ketene adducts, and 86 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 72% yield (0.24 mol).

EXAMPLE 18

The process of Example 1 was repeated except for increasing the molar ratio of each of dichloroacetyl chloride and triethylamine to isopropylcyclopentadiene in the second step.

To 281.2 g (3.6 mols) of dimethyl sulfoxide were added 49.3 g (0.72 mol) of cyclopentadiene (purity: 96.3%) and 39.6 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

To the cyclopentadienylpotassium solution was added 140.0 g of n-hexane, after which 147.4 g (1.2 mols) of isopropyl bromide was added dropwise over a period of 50 minutes while maintaining the solution temperature at 5° C. After completion of the dropwise addition, 1N hydrochloric acid and n-hexane were added and then the organic layer was separated to obtain 309 g of a n-hexane solution containing isopropylcyclopentadiene.

The n-hexane solution was analyzed by a gas chromatography to find that the yield of isopropylcyclopentadiene was 90.0% (0.54 mol) and that the ratio among its isomers was as follows: 1-isomer:5-isomer:2-isomer=29.2:63.0:7.8.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=91.1:1.1:7.8.

To the n-hexane solution was added 180 g of n-hexane to obtain 489 g of a n-hexane solution containing 58.3 g (0.54 mol) of isopropylcyclopentadiene. To this n-hexane solution was added 159.8 g (1.1 mols) of dichloroacetyl chloride, after which 114.6 g (1.1 mols) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 87% (0.47 mol).

The n-hexane was distilled off from the n-hexane solution containing the ketene adducts, and the residue was distilled under reduced pressure to obtain 97.2 g (0.41 mol) of a distillate containing the ketene adducts (purity: 93%). The ketene adducts were analyzed by a gas chromatography to find that the ratio among the ketene adducts derived from 1-isomer, 5-isomer and 2-isomer, respectively, of isopropylcyclopentadiene was 92.2:0.1:7.7.

A mixed solvent consisting of 25 g of acetic acid, 312 g of acetone and 52 g of water was added to the distillate containing the ketene adducts, and 104 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 68% yield (0.28 mol).

EXAMPLE 19

The process of Example 1 was repeated except for using no acetic acid in the third step.

To 281.0 g (3.6 mols) of dimethyl sulfoxide were added 49.0 g (0.71 mol) of cyclopentadiene (purity: 96.3%) and 39.7 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

To the cyclopentadienylpotassium solution was added 140.0 g of n-hexane, after which 147.8 g (1.2 mols) of isopropyl bromide was added dropwise over a period of 50 minutes while maintaining the solution temperature at 5° C. After completion of the dropwise addition, 1N hydrochloric acid and n-hexane were added and then the organic layer was separated to obtain 310 g of a n-hexane solution containing isopropylcyclopentadiene.

The n-hexane solution was analyzed by a gas chromatography to find that the yield of isopropylcyclopentadiene was 87.5% (0.53 mol) and that the ratio among its isomers was as follows: 1-isomer:5-isomer:2-isomer=27.5:64.8:7.7.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=91.3:1.0:7.7.

To the n-hexane solution was added 241 g of n-hexane to obtain 551 g of a n-hexane solution containing 57.0 g (0.53 mol) of isopropylcyclopentadiene. To this n-hexane solution was added 81.5 g (0.55 mol) of dichloroacetyl chloride, after which 58.6 g (0.58 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 82% (0.43 mol).

The n-hexane was distilled off from the n-hexane solution containing the ketene adducts, and the residue was distilled under reduced pressure to obtain 90.4 g (0.38 mol) of a distillate containing the ketene adducts (purity: 92%). The ketene adducts were analyzed by a gas chromatography to find that the ratio among the ketene adducts derived from 1-isomer, 5-isomer and 2-isomer, respectively, of isopropylcyclopentadiene was 99.8:0:0.2.

A mixed solvent consisting of 287 g of acetone and 48 g of water was added to the distillate containing the ketene adducts, and 96 g of triethylamine was added dropwise over a period of 2 hours while maintaining the solution temperature at 60° C. Then, the resulting mixture was heated at 60° C. for another 2.5 hours. After completion of the reaction, analysis by a gas chromatography revealed that peaks due to the ketene adducts disappeared and that hinokitiol was obtained in 52% yield (0.20 mol).

EXAMPLE 20

The process of Example 1 was repeated except that in the third step, triethylamine was charged all at once, but not dropwise.

To 281.0 g (3.6 mols) of dimethyl sulfoxide were added 49.5 g (0.72 mol) of cyclopentadiene (purity: 96.3%) and 39.2 g (0.59 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

To the cyclopentadienylpotassium solution was added 140.0 g of n-hexane, after which 147.1 g (1.2 mols) of isopropyl bromide was added dropwise over a period of 50 minutes while maintaining the solution temperature at 5° C. After completion of the dropwise addition, 1N hydrochloric acid and n-hexane were added and then the organic layer was separated to obtain 306 g of a n-hexane solution containing isopropylcyclopentadiene.

The n-hexane solution was analyzed by a gas chromatography to find that the yield of isopropylcyclopentadiene was 90.3% (0.54 mol) and that the ratio among its isomers was as follows: 1-isomer:5-isomer:2-isomer=26.8:65.4:7.8.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=91.2:1.0:7.8.

To the n-hexane solution was added 256 g of n-hexane to obtain 562 g of a n-hexane solution containing 58.0 g (0.54 mol) of isopropylcyclopentadiene. To this n-hexane solution was added 83.0 g (0.56 mol) of dichloroacetyl chloride, after which 59.7 g (0.59 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 81.5% (0.44 mol).

The n-hexane was distilled off from the n-hexane solution containing the ketene adducts, and the residue was distilled under reduced pressure to obtain 89.6 g (0.39 mol) of a distillate containing the ketene adducts (purity: 94%). The ketene adducts were analyzed by a gas chromatography to find that the ratio among the ketene adducts derived from 1-isomer, 5-isomer and 2-isomer, respectively, of isopropylcyclopentadiene was 99.8:0:0.2.

A mixed solvent consisting of 23 g of acetic acid, 97 g of triethylamine, 290 g of acetone and 48 g of water was added to the distillate containing the ketene adducts, and the resulting mixture was heated at 60° C. for 8 hours. After completion of the reaction, analysis by a gas chromatography revealed that peaks due to the ketene adducts disappeared and that hinokitiol was obtained in 67% yield (0.26 mol).

EXAMPLE 21

The process of Example 1 was repeated except for using t-butanol in place of acetone in the third step.

To 281.5 g (3.6 mols) of dimethyl sulfoxide were added 49.4 g (0.72 mol) of cyclopentadiene (purity: 96.3%) and 39.5 g (0.60 mol) of potassium hydroxide (purity: 85%), and the resulting mixture was stirred for 1.5 hours in a nitrogen stream at room temperature to obtain a cyclopentadienylpotassium solution. The molar ratio of dimethyl sulfoxide to cyclopentadienylpotassium was 6.0.

To the cyclopentadienylpotassium solution was added 140.0 g of n-hexane, after which 147.4 g (1.2 mols) of isopropyl bromide was added dropwise over a period of 50 minutes while maintaining the solution temperature at 5° C. After completion of the dropwise addition, 1N hydrochloric acid and n-hexane were added and then the organic layer was separated to obtain 308 g of a n-hexane solution containing isopropylcyclopentadiene.

The n-hexane solution was analyzed by a gas chromatography to find that the yield of isopropylcyclopentadiene was 91.0% (0.54 mol) and that the ratio among its isomers was as follows: 1-isomer:5-isomer:2-isomer=27.2:65.1:7.7.

The 5-isomer was isomerized to 1-isomer by allowing the n-hexane solution containing isopropylcyclopentadiene, to stand at 20° C. for 7 hours. The ratio among the isomers after the isomerization was as follows: 1-isomer:5-isomer:2-isomer=91.3:1.0:7.7.

To the n-hexane solution was added 262 g of n-hexane to obtain 570 g of a n-hexane solution containing 58.9 g (0.54 mol) of isopropylcyclopentadiene. To this n-hexane solution was added 84.3 g (0.57 mol) of dichloroacetyl chloride, after which 60.6 g (0.60 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 81.7% (0.44 mol).

The n-hexane was distilled off from the n-hexane solution containing the ketene adducts, and the residue was distilled under reduced pressure to obtain 92.2 g (0.39 mol) of a distillate containing the ketene adducts (purity: 93%). The ketene adducts were analyzed by a gas chromatography to find that the ratio among the ketene adducts derived from 1-isomer, 5-isomer and 2-isomer, respectively, of isopropylcyclopentadiene was 99.8:0:0.2.

A mixed solvent consisting of 24 g of acetic acid, 377 g of t-butanol and 49 g of water was added to the distillate containing the ketene adducts, and 99 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 66% yield (0.26 mol).

EXAMPLE 22

The process of Example 1 was repeated except for using potassium ethoxide in place of potassium hydroxide in the preparation of cyclopentadienyl metal.

To 562.5 g (7.2 mols) of dimethyl sulfoxide were added 49.4 g (0.72 mol) of cyclopentadiene (purity: 96.3%) and 53.1 g (0.60 mol) of potassium ethoxide (purity: 95%), and the resulting mixture was stirred for 40 minutes in a nitrogen stream at room temperature to obtain a cyclopentadienylpotassium solution. Potassium ethoxide was more reactive than potassium hydroxide. The molar ratio of dimethyl sulfoxide to cyclopentadienylpotassium was 12.0.

To the cyclopentadienylsodium solution was added 140.0 g of n-hexane, after which 147.5 g (1.2 mols) of isopropyl bromide was added dropwise over a period of 50 minutes while maintaining the solution temperature at 5° C. After completion of the dropwise addition, the salt formed was dissolved by adding 1N hydrochloric acid, and then the organic layer was separated to obtain 307 g of a n-hexane solution containing isopropylcyclopentadiene.

The n-hexane solution was analyzed by a gas chromatography to find that the yield of isopropylcyclopentadiene was 74.0% (0.44 mol) and that the ratio among its isomers was as follows: 1-isomer:5-isomer:2-isomer=47.6:38.3:14.1.

The 5-isomer was isomerized to 1-isomer by allowing the n-hexane solution containing isopropylcyclopentadiene, to stand at 20° C. for 6 hours. The ratio among the isomers after the isomerization was as follows: 1-isomer:5-isomer:2-isomer=85.0:0.9:14.1.

To the n-hexane solution was added 297 g of n-hexane to obtain 604 g of a n-hexane solution containing 47.5 g (0.44 mol) of isopropylcyclopentadiene. To this n-hexane solution was added 68.1 g (0.46 mol) of dichloroacetyl chloride, after which 49.0 g (0.48 mol) of triethylamine was added dropwise over a period of 2 hours while maintaining the solution temperature at 0° C. After completion of the dropwise addition, the salt formed was dissolved by adding 1N hydrochloric acid, and then the organic layer was separated to obtain a n-hexane solution containing ketene adducts.

The n-hexane solution containing ketene adducts was analyzed by a gas chromatography to find that the yield of the ketene adducts was 81% (0.36 mol).

The n-hexane was distilled off from the n-hexane solution containing the ketene adducts, and the residue was distilled under reduced pressure to obtain 73.9 g (0.32 mol) of a distillate containing the ketene adducts (purity: 93%). The distillate containing the ketene adducts was analyzed by a gas chromatography to find that the ratio among the adducts derived from 1-isomer, 5-isomer and 2-isomer, respectively, of isopropylcyclopentadiene was 98.3:0:1.7.

A mixed solvent consisting of 19 g of acetic acid, 239 g of acetone and 40 g of water was added to the distillate containing the ketene adducts, and 80 g of triethylamine was added dropwise over a period of 2 hours while maintaining the solution temperature at 60° C. Then, the resulting mixture was heated at 60° C. for another 5 hours. After completion of the reaction, analysis by a gas chromatography revealed that peaks due to the ketene adducts disappeared and that hinokitiol was obtained in 72% yield (0.23 mol).

PREPARATION EXAMPLE 1

The process of Example 1 was repeated, except that in the isopropylation step, potassium hydroxide was replaced by lithium hydroxide monohydrate.

To 280 g (3.6 mols) of dimethyl sulfoxide were added 49.3 g (0.72 mol) of cyclopentadiene (purity: 96.8%) and 25.18 g (0.60 mol) of lithium hydroxide monohydrate, and the resulting mixture was stirred for 1.5 hours in a nitrogen stream at room temperature to obtain a cyclopentadienyllithium solution. The molar ratio of dimethyl sulfoxide to cyclopentadienyllithium was 6.0.

To the cyclopentadienyllithium solution was added 139.5 g of n-hexane, after which 147.6 g (1.2 mols) of isopropyl bromide was added dropwise over a period of 50 minutes while maintaining the solution temperature at 5° C. After completion of the dropwise addition, the salt formed was dissolved by adding 1N hydrochloric acid, and then the organic layer was separated to obtain a n-hexane solution containing isopropylcyclopentadiene.

The n-hexane solution was analyzed by a gas chromatography to find that the ratio among its isomers was as follows: 1-isomer:5-isomer:2-isomer=21.5:75.2:3.3.

PREPARATION EXAMPLE 2

The process of Example 1 was repeated, except that in the isopropylation step, potassium hydroxide was replaced by rubidium hydroxide.

To 22.6 g (0.29 mols) of dimethyl sulfoxide were added 4.05 g (0.059 mol) of cyclopentadiene (purity: 96.8%) and 4.92 g (0.048 mol) of rubidium hydroxide, and the resulting mixture was stirred for 2 hours in a nitrogen stream at room temperature to obtain a cyclopentadienylrubidium solution. The molar ratio of dimethyl sulfoxide to cyclopentadienylrubidium was 6.0.

To the cyclopentadienylrubidium solution was added 11.31 g of n-hexane, after which 11.81 g (0.096 mol) of isopropyl bromide was added dropwise over a period of 50 minutes while maintaining the solution temperature at 5° C. After completion of the dropwise addition, the salt formed was dissolved by adding 1N hydrochloric acid, and then the organic layer was separated to obtain a n-hexane solution containing isopropylcyclopentadiene.

The n-hexane solution was analyzed by a gas chromatography to find that the ratio among its isomers was as follows: 1-isomer:5-isomer:2-isomer=24.0:54.6:21.3.

PREPARATION EXAMPLE 3

The process of Example 1 was repeated, except that in the isopropylation step, potassium hydroxide was replaced by caesium hydroxide monohydrate.

To 280 g (3.6 mols) of dimethyl sulfoxide were added 49.3 g (0.72 mol) of cyclopentadiene (purity: 96.8%) and 100.76 g (0.60 mol) of caesium hydroxide monohydrate, and the resulting mixture was stirred for 1.5 hours in a nitrogen stream at room temperature to obtain a cyclopentadienylcaesium solution. The molar ratio of dimethyl sulfoxide to cyclopentadienylcaesium was 6.0.

To the cyclopentadienylcaesium solution was added 140.0 g of n-hexane, after which 147.6 g (1.2 mols) of isopropyl bromide was added dropwise over a period of 50 minutes while maintaining the solution temperature at 5° C. After completion of the dropwise addition, the salt formed was dissolved by adding IN hydrochloric acid, and then the organic layer was separated to obtain a n-hexane solution containing isopropylcyclopentadiene.

The n-hexane solution was analyzed by a gas chromatography to find that the ratio among its isomers was as follows: 1-isomer:5-isomer:2-isomer=39.1:54.0:6.9.

COMPARATIVE EXAMPLE 1

There is described below a case where isopropylation was carried out without addition of an aliphatic hydrocarbon by using acetonitrile, an aprotic polar solvent homogeneously miscible with isopropylcyclopentadiene.

To 151.4 g (3.69 mols) of acetonitrile were added 15.9 g (0.23 mol) of cyclopentadiene (purity: 96.1%) and 12.5 g (0.19 mol) of potassium hydroxide (purity: 85%), and the resulting mixture was stirred for 3.5 hours in a nitrogen stream at room temperature and then heated at 55° C for 2 hours to obtain a cyclopentadienylpotassium solution. The molar ratio of acetonitrile to cyclopentadienylpotassium was 19.4.

The above-mentioned cyclopentadienylpotassium solution was added dropwise to 47.5 g (0.39 mol) of isopropyl bromide over a period of 120 minutes while maintaining the solution temperature at 5° C. After completion of the dropwise addition, 1N hydrochloric acid and n-hexane were added and then the organic layer was separated to obtain a n-hexane solution containing isopropylcyclopentadiene.

The n-hexane solution was analyzed by a gas chromatography to find that the yield of isopropylcyclopentadiene was 47.0% (0.089 mol) and that the ratio among its isomers was as follows: 1-isomer:5-isomer:2-isomer=44.3:0.5:55.2.

COMPARATIVE EXAMPLE 2

There is described below a case where isopropylation was carried out without addition of an aliphatic hydrocarbon by using tetrahydrofuran, an aprotic polar solvent homogeneously miscible with isopropylcyclopentadiene.

To 180.3 g (2.50 mols) of tetrahydrofuran were added 19.08 g (0.28 mol) of cyclopentadiene (purity: 96.1%) and 14.92 g (0.23 mol) of potassium hydroxide (purity: 85%), and the resulting mixture was stirred for 2 hours in a nitrogen stream at room temperature, but no cyclopentadienylpotassium was produced at all. When the mixture was heated at 45° C. for 1 hour and then 65° C. for 1 hour after the stirring, an insoluble material was formed. After the mixture was filtered, the filtrate was analyzed to find that cyclopentadienylpotassium was produced in an amount of only 0.4% based on the amount of KOH used.

The molar ratio of tetrahydrofuran to KOH employed above was 10.9.

The above-mentioned filtrate was added dropwise to 56.6 g (0.46 mol) of isopropyl bromide over a period of 60 minutes while maintaining the solution temperature at 5° C. After completion of the dropwise addition, 1N hydrochloric acid and n-hexane were added and then the organic layer was separated to obtain a n-hexane solution.

The n-hexane solution was analyzed by a gas chromatography to find that no isopropylcyclopentadiene was produced at all.

COMPARATIVE EXAMPLE 3

There is described below a case where isopropylation was carried out by using a solvent other than aprotic polar solvents.

To 96.0 g (1.1 mols) of n-hexane were added 15.1 g (0.22 mol) of cyclopentadiene (purity: 96.1%) and 12.5 g (0.19 mol) of potassium hydroxide (purity: 85%), and the resulting mixture was stirred for 3 hours in a nitrogen stream at room temperature, but no cyclopentadienylpotassium was produced at all.

COMPARATIVE EXAMPLE 4

There is described below another case where isopropylation was carried out by using a solvent other than aprotic polar solvents.

To 52.0 g (1.1 mols) of ethanol were added 15.6 g (0.23 mol) of cyclopentadiene (purity: 96.1%) and 12.5 g (0.19 mol) of potassium hydroxide (purity: 85%), and the resulting mixture was stirred for 3 hours in a nitrogen stream at room temperature to obtain a cyclopentadienylpotassium solution. The molar ratio of ethanol to cyclopentadienylpotassium was 6.0.

To the above-mentioned cyclopentadienylpotassium solution was added dropwise 47.0 g (0.38 mol) of isopropyl bromide over a period of 120 minutes while maintaining the solution temperature at 5° C. After completion of the dropwise addition, 1N hydrochloric acid and n-hexane were added and then the organic layer was separated.

The organic layer was analyzed by a gas chromatography to find that no isopropylcyclopentadiene was produced at all.

COMPARATIVE EXAMPLE 5

There is described below a case where isopropylation was carried out by using an aliphatic hydrocarbon and dimethylformamide, an aprotic polar solvent homogeneously miscible with isopropylcyclopentadiene.

To 264.4 g (3.6 mols) of dimethylformamide were added 50.2 g (0.73 mol) of cyclopentadiene (purity: 96.0%) and 39.6 g (0.60 mol) of potassium hydroxide (purity: 85%), and the resulting mixture was stirred at 30° C. for 2.5 hours in a nitrogen stream to obtain a cyclopentadienylpotassium solution. The molar ratio of dimethylformamide to cyclopentadienylpotassium was 6.0.

To the cyclopentadienylpotassium solution was added 139.3 g of n-hexane, after which 147.6 g (1.2 mols) of isopropyl bromide was added dropwise over a period of 60 minutes while maintaining the solution temperature at 5° C. After completion of the dropwise addition, 1N hydrochloric acid and n-hexane were added and then the organic layer was separated to obtain a n-hexane solution containing isopropylcyclopentadiene.

The n-hexane solution was analyzed by a gas chromatography to find that the yield of isopropylcyclopentadiene was 89.2% (0.54 mol) and that the ratio among its isomers was as follows: 1-isomer:5-isomer:2-isomer=40.7:0.3:59.0.

COMPARATIVE EXAMPLE 6

There is described below a case where isopropylation was carried out by using an aliphatic hydrocarbon and 1,3-dimethyl-2-imidazolidinone, an aprotic polar solvent homogeneously miscible with isopropylcyclopentadiene.

To 410.9 g (3.6 mols) of 1,3-dimethyl-2-imidazolidinone were added 51.1 g (0.74 mol) of cyclopentadiene (purity: 96.0%) and 39.7 g (0.60 mol) of potassium hydroxide (purity: 85%), and the resulting mixture was stirred for 1.5 hours in a nitrogen stream at room temperature to obtain a cyclopentadienylpotassium solution. The molar ratio of 1,3-dimethyl-2-imidazolidinone to cyclopentadienylpotassium was 6.0.

To the cyclopentadienylpotassium solution was added 141.3 g of n-hexane, after which 147.5 g (1.2 mols) of isopropyl bromide was added dropwise over a period of 60 minutes while maintaining the solution temperature at 5° C. After completion of the dropwise addition, 1N hydrochloric acid and n-hexane were added and then the organic layer was separated to obtain a n-hexane solution containing isopropylcyclopentadiene.

The n-hexane solution was analyzed by a gas chromatography to find that the yield of isopropylcyclopentadiene was 86.7% (0.52 mol) and that the ratio among its isomers was as follows: 1-isomer:5-isomer:2-isomer=40.1:1.7:58.2.

COMPARATIVE EXAMPLE 7

There is described below a case where isopropylation was carried out without addition of an aliphatic hydrocarbon by using tetrahydrofuran, an aprotic polar solvent homogeneously miscible with isopropylcyclopentadiene, according to prior art.

To 34.4 g (0.28 mol) of isopropyl bromide was added dropwise cyclopentadienylsodium (0.14 mol, a 2 M tetrahydrofuran solution; Aldrich Chemical Co.) over a period of 7 hours while maintaining the solution temperature at 2° C. After completion of the dropwise addition, 1N hydrochloric acid and n-hexane were added and then the organic layer was separated to obtain a n-hexane solution containing isopropylcyclopentadiene.

The n-hexane solution was analyzed by a gas chromatography to find that the yield of isopropylcyclopentadiene was 60.3% (0.084 mol) and that the ratio among its isomers was as follows: 1-isomer:5-isomer:2-isomer=40.9:0.7:58.4.

COMPARATIVE EXAMPLE 8

There is described below a case where isopropylation was carried out without addition of an aliphatic hydrocarbon by using tetrahydrofuran, an aprotic polar solvent homogeneously miscible with isopropylcyclopentadiene. This comparative example was carried out with reference to the descriptions in Examples of the prior art (xiii) and (xiv).

3.6 Grams (0.09 mol) of sodium hydride (oil dispersion, purity 60%) was washed with n-hexane and then refluxed in the presence of aluminum lithium hydride, and 40 ml of dried tetrahydrofuran was added, after which 9.2 g (0.14 mol) of cyclopentadiene (purity: 97.8%) was added dropwise over a period of 1 hour while maintaining the solution temperature at 5° C., to obtain a cyclopentadienylsodium solution.

To the cyclopentadienylsodium solution was added dropwise 13.2 g (0.11 mol) of isopropyl bromide over a period of 40 minutes while maintaining the solution temperature at −50° C. After completion of the dropwise addition, the resulting solution was heated to 0° C over a period of 1 hour. A small volume of this solution was sampled, treated with 1N hydrochloric acid and n-hexane, and then analyzed by a gas chromatography to find that the yield of isopropylcyclopentadiene was 7.9% and that the ratio among its isomers was as follows: 1-isomer 5-isomer:2-isomer=40.9:3.1:56.0.

After the heated solution was stirred for 2 hours while maintaining the solution at 0° C, 1N hydrochloric acid and n-hexane were added and then the organic layer was separated to obtain a n-hexane solution containing isopropylcyclopentadiene.

The n-hexane solution was analyzed by a gas chromatography to find that the yield of isopropylcyclopentadiene was 58.3% (0.053 mol) and that the ratio among its isomers was as follows: 1-isomer:5-isomer:2-isomer=41.3:2.9:55.9.

Industrial Applicability

By the process of the present invention, 1-isopropylcyclopentadiene can be obtained from cyclopentadiene with high selectivity at low cost by a simple procedure without extreme nonaqueous conditions. Using this 1-isopropylcyclopentadiene, very industrially advantageous production of hinokitiol can be achieved.

What is claimed is:

1. A process for producing hinokitiol which comprises the step of obtaining 1-isopropylcyclopentadiene from cyclopentadiene and an isopropylating agent represented by the general formula R—X wherein R is an isopropyl group and X is a halogen atom, a tosyl group or an alkylsulfonate group (first step), reacting the 1-isopropylcyclopentadiene with a dihaloketene to obtain a ketene adduct (second step), and decomposing the ketene adduct (third step), said first step comprising the following three steps:
   a) a step of preparing a cyclopentadienyl metal from cyclopentadiene and at least one of a metal hydroxide or a metal alkoxide (preparation step of cyclopentadienyl metal);
   b) a step of obtaining isopropylcyclopentadiene by reacting the cyclopentadienyl metal with the isopropylating agent in the presence of an aprotic polar solvent capable of forming two liquid phases when mixed with isopropylcyclopentadiene as a product (isopropylation step); and
   c) a step of isomerizing 5-isopropylcyclopentadiene in the isopropylcyclopentadiene selectively to 1-isopropylcyclopentadiene with heat (isomerization step).

2. A process according to claim 1, which further comprises a step of separating a phase composed mainly of isopropylcyclopentadiene, by taking out a lower layer after standing after the isopropylation step.

3. A process according to claim 1, wherein said aprotic polar solvent is dimethyl sulfoxide in the isopropylation step.

4. A process according to claim 1, wherein the metal hydroxide is used in the preparation step of cyclopentadienyl metal.

5. A process according to claim 1, wherein the metal hydroxide is potassium hydroxide in the preparation step of cyclopentadienyl metal.

6. A process according to claim 1, wherein the isopropylation step is carried out in the presence of an aliphatic hydrocarbon in addition to said aprotic polar solvent.

7. A process according to claim 1, wherein said aprotic polar solvent is used in an amount of 4 moles or more per mole of the cyclopentadienyl metal in the isopropylation step.

8. A process according to claim 1, wherein said aprotic polar solvent is used in an amount of 6 moles or more per mole of the cyclopentadienyl metal in the isopropylation step.

9. A process according to claim 1, wherein in the isopropylation step, said aprotic polar solvent is used in an amount of 10 moles or more per mole of the cyclopentadienyl metal, and a solution containing the cyclopentadienyl metal is added to the isopropylating agent.

10. A process according to claim 1, wherein in the isopropylation step, said metal alkoxide is potassium ethoxide and said aprotic polar solvent is used in an amount of 12 moles or more per mole of the cyclopentadienyl metal.

11. A process according to claim 1, wherein a reaction temperature is not higher than 30° C. in the isopropylation step.

12. A process according claim 1, wherein an amount of water present in the reaction system is not more than 3 moles per mole of the cyclopentadienyl metal in the isopropylation step.

13. A process according to claim 1, wherein the preparation step of cyclopentadienyl metal and the isopropylation step are carried out in an inert gas atmosphere.

14. A process according to claim 1, wherein a temperature at the isomerization step is 0C to 40° C.

15. A process according to claim 1, wherein in the third step, the decomposition of the ketene adduct is carried out in the presence of triethylamine, water and a hydrophilic organic solvent while adding triethylamine dropwise to the reaction system.

16. A process according to claim 13, wherein the decomposition of the ketene adduct is carried out by further adding at least one organic acid selected from the group consisting of formic acid, acetic acid and propionic acid.

17. A process according to claim 13, wherein said water-soluble organic solvent is tertiary butanol.

18. A process according to claim 1, wherein a portion of an apparatus used in the third step and a hinokitiol purification step which is brought into contact with hinokitiol is made of at least one material selected from the group consisting of Hastelloy C, glass, resins and ceramics.

* * * * *